US010280234B2

(12) United States Patent
Crowther et al.

(10) Patent No.: US 10,280,234 B2
(45) Date of Patent: May 7, 2019

(54) CATALYST COMPOSITIONS AND USE THEREOF

(71) Applicant: ExxonMobil Chemical Patents Inc., Baytown, TX (US)

(72) Inventors: Donna J. Crowther, Blairsville, GA (US); Hua Zhou, Houston, TX (US); Jacqueline A. Lovell, Crosby, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/782,418

(22) Filed: Oct. 12, 2017

(65) Prior Publication Data

US 2018/0134817 A1 May 17, 2018

Related U.S. Application Data

(60) Provisional application No. 62/420,816, filed on Nov. 11, 2016.

(51) Int. Cl.
| | |
|---|---|
| *C08F 4/64* | (2006.01) |
| *B01J 31/22* | (2006.01) |
| *C07F 7/00* | (2006.01) |
| *C07F 7/30* | (2006.01) |
| *C08F 210/16* | (2006.01) |
| *C07F 7/18* | (2006.01) |
| *C08F 10/00* | (2006.01) |
| *C08F 4/659* | (2006.01) |

(52) U.S. Cl.
CPC ......... *C08F 4/64182* (2013.01); *B01J 31/223* (2013.01); *C07F 7/003* (2013.01); *C07F 7/1804* (2013.01); *C07F 7/30* (2013.01); *C08F 210/16* (2013.01); *C08F 4/659* (2013.01); *C08F 4/65908* (2013.01); *C08F 4/65912* (2013.01); *C08F 10/00* (2013.01)

(58) Field of Classification Search
None
See application file for complete search history.

(56) References Cited

U.S. PATENT DOCUMENTS

| | | |
|---|---|---|
| 5,889,134 A | 3/1999 | Pu et al. |
| 6,020,452 A | 2/2000 | Pu et al. |
| 6,841,502 B2 | 1/2005 | Boussie et al. |
| 6,869,904 B2 | 3/2005 | Boussie et al. |
| 6,897,276 B2 | 5/2005 | Boussie et al. |
| 7,030,256 B2 | 4/2006 | Boussie et al. |
| 7,060,848 B2 | 6/2006 | Boussie et al. |
| 7,091,292 B2 | 8/2006 | Boussie et al. |
| 7,126,031 B2 | 10/2006 | Boussie et al. |
| 7,241,714 B2 | 7/2007 | Boussie et al. |
| 7,241,715 B2 | 7/2007 | Boussie et al. |
| 7,659,415 B2 | 2/2010 | Boussie et al. |
| 8,058,373 B2 | 11/2011 | Stevens et al. |
| 8,420,847 B2 | 4/2013 | Terada et al. |
| 8,455,601 B2 | 6/2013 | Kolv et al. |
| 9,029,487 B2 | 5/2015 | Klosin et al. |
| 2006/0052554 A1 | 3/2006 | Boussie et al. |
| 2017/0306068 A1* | 10/2017 | Holtcamp ............. C08F 210/02 |
| 2018/0030167 A1 | 2/2018 | Atienza et al. |

FOREIGN PATENT DOCUMENTS

| | | |
|---|---|---|
| WO | 03/091262 | 11/2003 |
| WO | 2005/108406 | 11/2005 |
| WO | 2006/020624 | 2/2006 |
| WO | 2007/136493 | 11/2007 |
| WO | 2009/064482 | 5/2009 |
| WO | 2012/027448 | 3/2012 |
| WO | 2016/089935 | 6/2016 |
| WO | 2016/094861 | 6/2016 |
| WO | 2018/022238 | 2/2018 |

OTHER PUBLICATIONS

Van der Linden et al., "Polymerization of .alpha.-Olefins and Butadiene and Catalytic Cyclotrimerization of 1-Alkynes by a New Class of Group IV Catalysts. Control of Molecular Weight and Polymer Microstructure via Ligand Tuning in Sterically Hindered Chelating Phenoxide Titanium and Zirconium Species," Journal of the American Chemical Society, 1995, vol. 117, vol. 11, pp. 3008-3021.

Ihori et al., "Chiral Zirconium Catalysts Using Multidentate Binol Derivatives for Catalytic Enantioselective Mannich-Type Reactions; Ligand Optimization and Approaches to Elucidation of the Catalyst Structure," Journal of the American Chemical Society, 2005, vol. 127, No. 44, pp. 15528-15535.

Matsunaga et al., "Catalytic Enantioselective meso-Epoxide Ring Opening Reaction with Phenolic Oxygen Nucleophile Promoted by Gallium Heterobimetallic Multifunctional Complexes," Journal of the American Chemical Society, 2000, vol. 122, No. 10, pp. 2252-2260.

Kiesewetter et al., "Stereospecific Octahedral Group 4 Bis(phenolate) Ether Complexes for Olefin Polymerization," Journal of the American Chemical Society, 2010, vol. 132, No. 16, pp. 5566-5567.

Kayal et al., "Ortho-Linked Polyaryloxide Ligands and Their Titanium Complexes," Inorganic Chemistry, 2000, vol. 39, No. 16, pp. 3696-3704.

Huang et al., "From Highly Enantioselective Monomeric Catalysts to Highly Enantioselective Polymeric Catalysts: Application of Rigid and Sterically Regular Chiral Binaphthyl Polymers to the Asymmetric Synthesis of Chiral Secondary Alcohols," Journal of Organic Chemistry, 1999, vol. 64, No. 21, pp. 7940-7956.

Huang et al., "The First Highly Enantioselective Catalytic Diphenylzinc Additions to Aldehydes: Synthesis of Chiral Diarylcarbinols by Asymmetric Catalysis," Journal of Organic Chemistry, 1999, vol. 64, No. 12, pp. 4222-4223.

Turlington et al., "Catalytic Asymmetric Synthesis of Chiral Propargylic Alcohols for the Intramolecular Pauson—Khand Cycloaddition," Journal of Organic Chemistry, 2010, vol. 75, No. 20, pp. 6941-6952.

(Continued)

*Primary Examiner* — Catherine S Branch

(57) ABSTRACT

This invention relates to novel transition metal catalyst compounds comprising four oxygen atoms bonded to a transition metal where two of the oxygen groups are bonded to the metal by dative bonds and a silyl or germyl bridge, catalyst systems comprising such, and polymerization processes using such.

48 Claims, No Drawings

(56) References Cited

OTHER PUBLICATIONS

Fokken et al., "Nine-Membered Titanacyclic Complexes Based on an Ethylene-Bridged Bis(phenolato) Ligand: Synthesis, Structure, and Olefin Polymerization Activity," Organometallics, 1997, vol. 16, No. 20, pp. 4240-4242.
Brzezinski et al., "A cyclic hydrogen-bonded system with collective proton motion in bis(2,2'-dihydroxy-3-biphenylyl)methane," Journal of Physical Chemistry, 1993, vol. 97, No. 25, pp. 6590-6591.
Umare et al., "Polyethylene Waxes: Catalytic Synthesis by Ti-Biphenolates," Journal of Macromolecular Science, Part A, 2007, vol. 44, No. 9, pp. 977-987.
Brook, "Molecular rearrangements of organosilicon compounds," Accounts of Chemical Research, 1974, vol. 7, No. 3, pp. 77-84.
Vogl et al., "Linking Binol: C2-Symmetric Ligands for Investigations on Asymmetric Catalysis," Tetrahedron Letters, 1998, vol. 39, No. 43, pp. 7917-7920.
Ghose, "Synthesis of Some Carbon-functional Organosilicon Compounds," Journal of Organometallic Chemistry, 1979, vol. 164, No. 1, pp. 11-18.

\* cited by examiner

CATALYST COMPOSITIONS AND USE THEREOF

PRIORITY CLAIM

This application claims priority to and benefit of U.S. Ser. No. 62/420,816, field Nov. 11, 2016, which is incorporated by reference in its entirety.

FIELD OF THE INVENTION

This invention relates to novel transition metal catalyst compounds comprising four oxygen atoms bonded to a transition metal where two of the oxygen groups are bonded to the metal by dative bonds and bridged by a silyl or germanyl group, catalyst systems comprising such, and polymerization processes using such.

BACKGROUND OF THE INVENTION

Olefin polymerization catalysts are of great use in industry. Hence, there is interest in finding new catalyst systems that increase the commercial usefulness of the catalyst and allow the production of polymers having improved properties.

Journal of the American Chemical Society 1995, 117, 3008-3021, discloses bis-phenoxides without dative bonds.

Journal of the American Chemical Society (2005), 127 (44), 15528-15535, discloses compounds with no dative bonds.

WO 2003091262 and U.S. Pat. No. 7,060,848 disclose bridged bi-aromatic catalyst complexes typically bridged via two heteroatoms.

U.S. Pat. No. 8,058,373 discloses complexes represented by the formula:

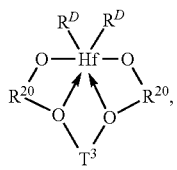

where $T^3$ is a divalent hydrocarbon or silane group having from 3 to 20 atoms not counting hydrogen, or an inertly substituted derivative thereof.

Other references of interest include: U.S. Pat. No. 8,420,847; WO 2012/027448; U.S. Pat. Nos. 9,029,487; 5,889,134; 6,020,452; US 2013/0144018; US 2004/0005984; US 2004/0010103; US 2004/0014950; U.S. Pat. Nos. 6,841,502; 6,869,904; US 2005/0080281; U.S. Pat. No. 6,897,276; US 2005/0164872; U.S. Pat. No. 7,030,256; US 2006/0211892; U.S. Pat. Nos. 7,126,031; 7,241,715; US 2008/0269470; U.S. Pat. No. 7,659,415; US 2006/0025548; US 2006/0052554; U.S. Pat. No. 7,091,292; US 2006/0205588; U.S. Pat. No. 7,241,714; Inorganic Chemistry (2000), 39(16), 3696-3704; Tetrahedron Letters (1998), 39(43), 7917-7920; Journal of Organic Chemistry (1999), 64(21), 7940-7956; Journal of the American Chemical Society (2000), 122(10), 2252-2260; Journal of Organic Chemistry (1999), 64(12), 4222-4223; Journal of Organic Chemistry (2010), 75(20), 6941-6952; Journal of Physical Chemistry (1993), 97(25), 6590-1; Brook, Acc. Chem. Res. 1974, 7, 77; Ghose, B., Journal of Organometallic Chemistry, 1979, 164(1), 11-18; Organomatallics, 1997, 16(20), 4240-4242; Journal of Macromolecular Science, Part A, Pure and Applied Chemistry (2007) 44, 977-987; and Journal of the American Chemical Society 2010, 132(16), 5566-5567.

There is still a need in the art for new and improved catalyst systems for the polymerization of olefins, in order to achieve specific polymer properties, such as low molecular weights, increased conversion or comonomer incorporation, or to alter comonomer distribution without deteriorating the resulting polymer's properties.

It is therefore an object of the present invention to novel catalyst compounds, catalysts systems comprising such compounds, and processes for the polymerization of olefins using such compounds and systems.

SUMMARY OF THE INVENTION

This invention relates to a catalyst compound represented by the formula:

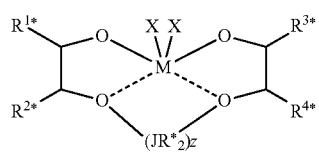

wherein
the dotted line indicates a dative bond;
M is a group 4 metal;
each J is, independently, Si or Ge, provided that when z is 2 or more one JR*s may be CR*$_2$;
z is a number from 1 to 12, provided that when z is 2, the two JR*2 groups may be connected by a heteroatom, X*, to form a group represented by the formula R*$_2$J-X*-JR*$_2$;
each of R$^{1*}$, R$^{2*}$, R$^{3*}$, R$^{4*}$, and R* is, independently, hydrogen, a substituted C$_1$ to C$_{40}$ hydrocarbyl group, a C$_1$ to C$_{40}$ unsubstituted hydrocarbyl group, or a heteroatom, provided that any adjacent R* groups may form a fused ring or multicenter fused ring system where the rings may be aromatic, partially saturated or saturated; and
each X is, independently, a substituted C$_1$ to C$_{40}$ hydrocarbyl group, a C$_1$ to C$_{40}$ unsubstituted hydrocarbyl group, a hydride, an amide, an alkoxide, a sulfide, a phosphide, a halide, an amine, a phosphine, an ether, a combination thereof, or two X's may form a part of a fused ring or a ring system.

This invention further relates to a catalyst compound represented by the formula:

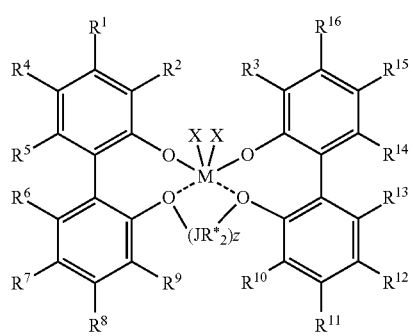

wherein
the dotted line indicates a dative bond;
M is a group 4 metal;
each J is, independently, Si or Ge, provided that when z is 2 or more one JR*s may be CR*$_2$;
z is a number from 1 to 12, provided that when z is 2, the two JR*2 groups may be connected by a heteroatom, X*, to form a group represented by the formula R*$_2$J-X*-JR*$_2$;
each of R*, R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$ and R$^{16}$ is, independently, hydrogen, a substituted C$_1$ to C$_{40}$ hydrocarbyl group, a C$_1$ to C$_{40}$ unsubstituted hydrocarbyl group, or a heteroatom, provided that any of adjacent R groups may form a fused ring or multicenter fused ring system where the rings may be aromatic, partially saturated or saturated; and
each X is, independently, a substituted C$_1$ to C$_{40}$ hydrocarbyl group, a C$_1$ to C$_{40}$ unsubstituted hydrocarbyl group, a hydride, an amide, an alkoxide, a sulfide, a phosphide, a halide, an amine, a phosphine, an ether, and a combination thereof, (two X's may form a part of a fused ring or a ring system).

This invention further relates to catalyst systems comprising the above catalyst compounds and an activator.

This invention also relates to a method to polymerize olefins comprising contacting the above catalyst compound with an activator and one or more monomers.

DETAILED DESCRIPTION OF THE INVENTION

For the purposes of this invention and the claims thereto, the new numbering scheme for the Periodic Table Groups is used as described in CHEMICAL AND ENGINEERING NEWS, 63(5), pg. 27 (1985). Therefore, a "group 4 metal" is an element from group 4 of the Periodic Table, e.g., Hf, Ti, Zr, or Rf.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, the olefin present in such polymer or copolymer is the polymerized form of the olefin. For example, when a copolymer is said to have an "ethylene" content of 35 wt % to 55 wt %, it is understood that a mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. Accordingly, the definition of copolymer, as used herein, includes terpolymers and the like. "Different" as used to refer to mer units indicates that the mer units differ from each other by at least one atom or are different isomerically. An "ethylene polymer" or "ethylene copolymer" is a polymer or copolymer comprising at least 50 mol % ethylene derived units, a "propylene polymer" or "propylene copolymer" is a polymer or copolymer comprising at least 50 mol % propylene derived units, a "butylene polymer" or "butylene copolymer" is a polymer or copolymer comprising at least 50 mol % butylene derived units, and so on.

For the purposes of this invention, ethylene shall be considered an α-olefin.

For purposes of this invention and claims thereto, unless otherwise indicated, the term "substituted" means that a hydrogen or carbon atom has been replaced with a heteroatom, or a heteroatom-containing group. For example, a "substituted hydrocarbyl" is a radical made of carbon and hydrogen where at least one hydrogen or carbon atom is replaced by a heteroatom or heteroatom-containing group, e.g., ethyl alcohol is an ethyl group substituted with an —OH group. Useful substituted hydrocarbyl radicals include radicals in which at least one hydrogen atom of the hydrocarbyl radical has been substituted with at least one halogen (such as Br, Cl, F, or I) or at least one functional group such as NR*$_2$, OR*, SeR*, TeR*, PR*$_2$, AsR*$_2$, SbR*$_2$, SR*, BR*$_2$, SiR*$_3$, GeR*$_3$, SnR*$_3$, PbR*$_3$, and the like, or where at least one heteroatom has been inserted within a hydrocarbyl ring.

As used herein, Mn is number average molecular weight, Mw is weight average molecular weight, and Mz is z average molecular weight, wt % is weight percent, and mol % is mole percent. Molecular weight distribution (MWD), also referred to as polydispersity index or polydispersity index (PDI), is defined to be Mw divided by Mn. Unless otherwise noted, all molecular weight units (e.g., Mw, Mn, Mz) are g/mol. The following abbreviations may be used herein: Me is methyl, Et is ethyl, Pr is propyl, cPR is cyclopropyl, nPr is n-propyl, iPr is isopropyl, Bu is butyl, nBu is normal butyl, iBu is isobutyl, sBu is sec-butyl, tBu is tert-butyl, Oct is octyl, MAO is methylalumoxane, dme is 1,2-dimethoxyethane, TMS is trimethylsilyl, TIBAL is tri-isobutylaluminum, TNOAL is tri(n-octyl)aluminum, p-Me is para-methyl, Ph is phenyl, Bn is benzyl (i.e., CH$_2$Ph), THF (also referred to as thf) is tetrahydrofuran, tol is toluene, EtOAc is ethyl acetate, and Cy is cyclohexyl.

A "catalyst system" is the combination of at least one catalyst compound, at least one activator, optional co-activator, and optional support material. For the purposes of this invention and the claims thereto, when catalyst systems are described as comprising neutral stable forms of the components, it is well understood by one of ordinary skill in the art, that the ionic form of the component is the form that reacts with the monomers to produce polymers.

In the description herein, the catalyst may be described as a catalyst precursor, a pre-catalyst compound, catalyst, catalyst compound, a transition metal compound, a transition metal complex, or a complex and these terms are used interchangeably. Activator and cocatalyst are also used interchangeably. An "anionic ligand" is a negatively charged ligand which donates one or more pairs of electrons to a metal ion. A "neutral donor ligand" is a neutrally charged ligand which donates one or more pairs of electrons to a metal ion.

For purposes of this invention and claims thereto in relation to transition metal catalyst compounds, the term "substituted" means that a hydrogen or carbon atom has been replaced with a hydrocarbyl group, a heteroatom, or a heteroatom-containing group. For example, methyl cyclopentadiene (Cp) is a Cp group substituted with a methyl group.

The terms "hydrocarbyl radical," "hydrocarbyl," "hydrocarbyl group," "alkyl radical," and "alkyl" are used interchangeably throughout this document. Likewise, the terms "group," "radical," and "substituent" are also used interchangeably in this document. For purposes of this disclosure, "hydrocarbyl radical" is defined to be C$_1$-C$_{100}$ radicals, that may be linear, branched, or cyclic, and when cyclic, aromatic or non-aromatic. Examples of such radicals include, but are not limited to, methyl, ethyl, n-propyl, isopropyl, n-butyl, isobutyl, sec-butyl, tert-butyl, pentyl, iso-amyl, hexyl, octyl cyclopropyl, cyclobutyl, cyclopentyl, cyclohexyl, cyclooctyl, and the like including their substituted analogues.

The term "alkenyl" means a straight-chain, branched-chain, or cyclic hydrocarbon radical having one or more double bonds. These alkenyl radicals may be optionally substituted. Examples of suitable alkenyl radicals include, but are not limited to, ethenyl, propenyl, allyl, 1,4-butadienyl cyclopropenyl, cyclobutenyl, cyclopentenyl, cyclohexenyl, cyclooctenyl and the like including their substituted analogues.

The term "aryl" or "aryl group" means a six carbon aromatic ring and the substituted variants thereof, including but not limited to, phenyl, 2-methyl-phenyl, xylyl, 4-bromo-xylyl. Likewise, heteroaryl means an aryl group where a ring carbon atom (or two or thee ring carbon atoms) has been replaced with a heteroatom, preferably N, O, or S. As used herein, the term "aromatic" also refers to pseudoaromatic heterocycles which are heterocyclic substituents that have similar properties and structures (nearly planar) to aromatic heterocyclic ligands, but are not by definition aromatic; likewise the term aromatic also refers to substituted aromatics.

A scavenger is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the transition metal compound to form an alkylated transition metal compound.

The term "continuous" means a system that operates without interruption or cessation. For example, a continuous process to produce a polymer would be one where the reactants are continually introduced into one or more reactors and polymer product is continually withdrawn.

A solution polymerization means a polymerization process in which the polymer is dissolved in a liquid polymerization medium, such as an inert solvent or monomer(s) or their blends. A homogeneous polymerization is one where the polymer product is dissolved in the polymerization medium. Such systems are preferably not turbid as described in J. Vladimir Oliveira, C. Dariva and J. C. Pinto, Ind. Eng. Chem. Res. 29, 2000, 4627. A solution polymerization is typically a homogeneous polymerization.

A bulk polymerization means a polymerization process in which the monomers and/or comonomers being polymerized are used as a solvent or diluent using little or no non-monomer inert solvent as a solvent or diluent. A small fraction of inert solvent might be used as a carrier for catalyst and scavenger. A bulk polymerization system contains less than 25 wt % of inert solvent or diluent, preferably less than 10 wt %, preferably less than 1 wt %, preferably 0 wt %.

Catalyst Compounds

The transition metal compounds descried herein are typically molecules in which an ancillary ligand is coordinated to a central transition metal atom. The ligand is bulky and stably bonded to the transition metal so as to maintain its influence during use of the catalyst, such as polymerization. The ligand may be coordinated to the transition metal by covalent bond and/or electron donation coordination or intermediate bonds. The transition metal compounds are generally subjected to activation to perform their polymerization or oligomerization function using an activator, which is believed to create a cation as a result of the removal of an anionic group, often referred to as a leaving group, from the transition metal.

This invention relates to catalyst compounds represented by the formula:

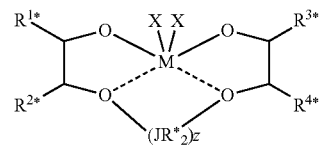

wherein
the dotted line indicates a dative bond;
M is a group 4 metal, preferably Ti, Hf, or Zr, preferably Hf or Zr;
each J is, independently, Si or Ge, provided that when z is 2 or more one $JR^*s$ may be $CR^*_2$;
z is a number from 1 to 12, provided that when z is 2, the two $JR^*2$ groups may be connected by a heteroatom, $X^*$, to form a group represented by the formula $R^*_2J-X^*-JR^*_2$;
preferably z is 1, 2, 3, 4, 5, 6, 7, 8, 9, 10, 11, or 12, preferably 1, 2, 3, 4, or 5;
each of $R^{1*}$, $R^{2*}$, $R^{3*}$, $R^{4*}$, and $R^*$ is, independently, hydrogen, a substituted $C_1$ to $C_{40}$ hydrocarbyl group, a $C_1$ to $C_{40}$ unsubstituted hydrocarbyl group, or a heteroatom, provided that any adjacent $R^*$ groups may form a fused ring or multicenter fused ring system where the rings may be aromatic, partially saturated or saturated; and
each X is, independently, a substituted $C_1$ to $C_{40}$ hydrocarbyl group, a $C_1$ to $C_{40}$ unsubstituted hydrocarbyl group, a hydride, an amide, an alkoxide, a sulfide, a phosphide, a halide, an amine, a phosphine, an ether, and a combination thereof, (two X's may form a part of a fused ring or a ring system), preferably each X is, independently, selected from halides (Cl, Br, F, I,) and $C_1$ to $C_5$ alkyl groups (e.g., methyl, ethyl, propyl, butyl, pentyl, or an isomer thereof), preferably each X is a dimethylamido, benzyl, or methyl group.

In a preferred embodiment this invention relates to a catalyst compound, and catalyst systems comprising such compounds, represented by the formula:

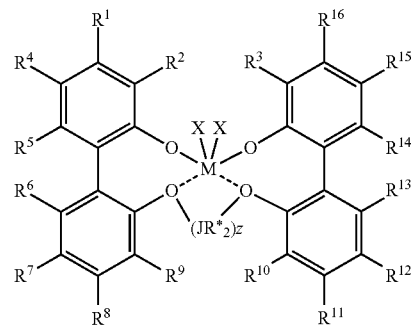

wherein:
the dotted line indicates a dative bond;
M is a group 4 metal, such as Hf, Zr, or Ti, preferably Ti;
each J is, independently, Si or Ge, provided that when z is 2 or more one $JR^*$ may be $CR^*_2$;
z is a number from 1 to 12, provided that when z is 2, the two $JR^*2$ groups may be connected by a heteroatom, $X^*$, to form a group represented by the formula $R^*_2J-X^*-JR^*_2$;

preferably z is 1, 2, 3, 4, 5, 6, 7, 8, 9, 10, 11, or 12, preferably 1, 2, 3, 4, or 5;

each of R*, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, hydrogen, a substituted $C_1$ to $C_{40}$ hydrocarbyl group, a $C_1$ to $C_{40}$ unsubstituted hydrocarbyl group, or a heteroatom, provided that any of adjacent R groups may form a fused ring or multicenter fused ring system where the rings may be aromatic, partially saturated, or saturated; and each X is, independently, a substituted $C_1$ to $C_{40}$ hydrocarbyl group, a $C_1$ to $C_{40}$ unsubstituted hydrocarbyl group, a hydride, an amide, an alkoxide, a sulfide, a phosphide, a halide, an amine, a phosphine, an ether, and a combination thereof, (two X's may form a part of a fused ring or a ring system), preferably each X is, independently, selected from halides (Cl, Br, F, I,) and $C_1$ to $C_5$ alkyl groups (e.g., methyl, ethyl, propyl, butyl, pentyl, or an isomer thereof), preferably each X is a dimethylamido, benzyl, or methyl group.

In a preferred embodiment of the invention, each R*, $R^{1*}$, $R^{2*}$, $R^{3*}$, $R^{4*}$, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, hydrogen, methyl, ethyl, propyl, butyl, pentyl, hexyl, heptyl, octyl, nonyl, decyl, undecyl, docecyl, t-butyl, isopropyl, phenyl, napthyl, or an isomer thereof.

In a preferred embodiment of the invention, each R* is, independently, methyl, ethyl, propyl, butyl, pentyl, hexyl, heptyl, octyl, nonyl, decyl, undecyl, docecyl, t-butyl, isopropyl, phenyl, napthyl, or an isomer thereof and z is 1, 2, 3, 4, or 5.

In a preferred embodiment of the invention, each R* is, independently, cyclobutyl, cyclopentyl, cyclopropyl, cyclohexyl, silacyclobutyl, silacyclopropyl, germacyclobutyl, germacyclopropyl, phenyl, napthyl, or a substituted version thereof and z is 1, 2, 3, 4, or 5 (preferably 1).

In a preferred embodiment of the invention, the $(JR*_2)z$ group comprises one or more of dicyclohexylsilyl, diphenylsilyl, di3',5'-di-tert-butylphenylsilyl, dicarbazolylsilyl, difluorenlylsilyl, cyclobutylsilyl, dicyclobutylsilyl, dicyclohexylgermyl, diphenylgermyl, di3',5'-di-tert-butylphenylgermyl, dicarbazolylgermyl, difluorenylgermyl, cyclobutylgermyl, dicyclobutylgermyl, (dicyclohexylsilyl)$_2$, (diphenylsilyl)$_2$, (di3',5'-di-tert-butylphenylsilyl)$_2$, (dicarbazolylsilyl))$_2$, (difluorenylsilyl)$_2$, (cyclobutylsilyl)$_2$, (dicyclobutylsilyl)$_2$, (dicyclohexylgermyl)$_2$, (diphenylgermyl)$_2$, (di3',5'-di-tert-butylphenylgermyl)$_2$, (dicarbazolylgermyl)$_2$, (difluorenylgermyl)$_2$, (cyclobutylgermyl)$_2$, and (dicyclobutylgermyl)$_2$.

In a preferred embodiment of the invention, X* is represented by the formula QR*v, where Q is the heteroatom, R* is as described above, and v is the valence state of the heteroatom minus 2 (e.g., 2, 3, or 4), preferably X* is a group 14, 15, or 16 heteroatom, preferably X* is O, S, $NR*_2$, or $PR*_2$.

Particularly useful catalyst compounds include those represented by one or more of the formulas:

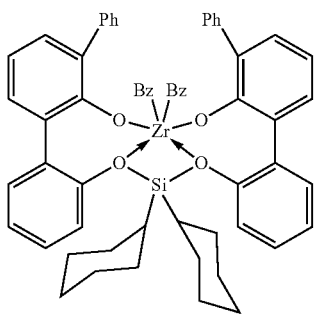

-continued

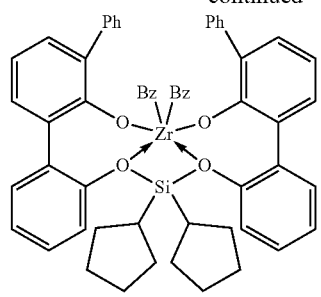

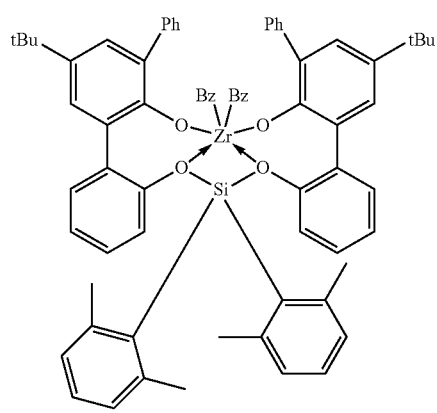

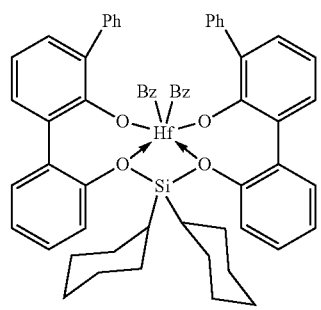

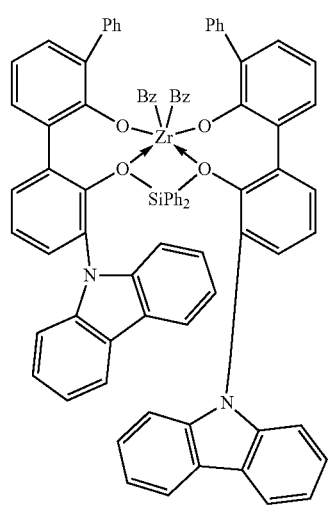

-continued

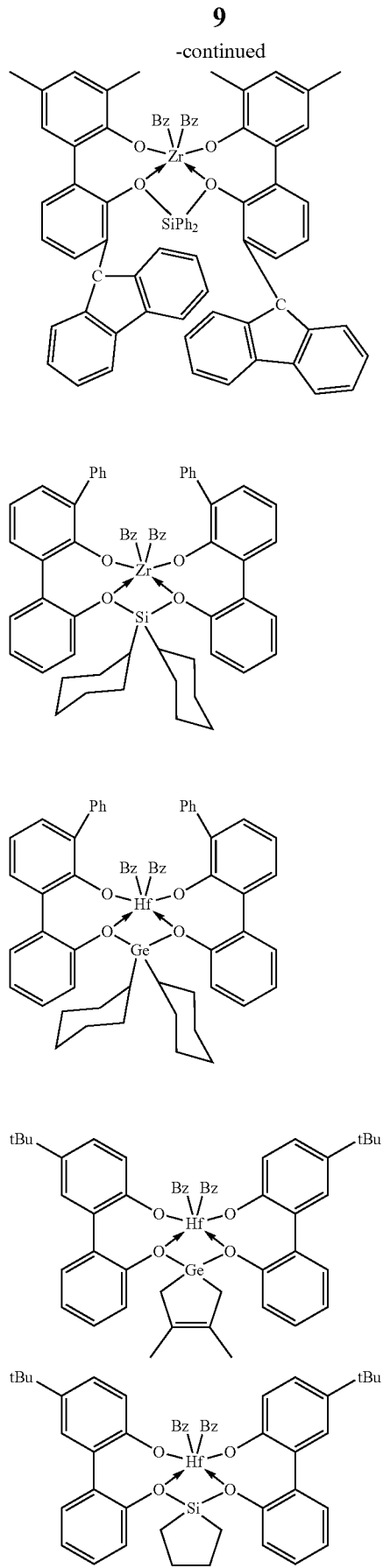
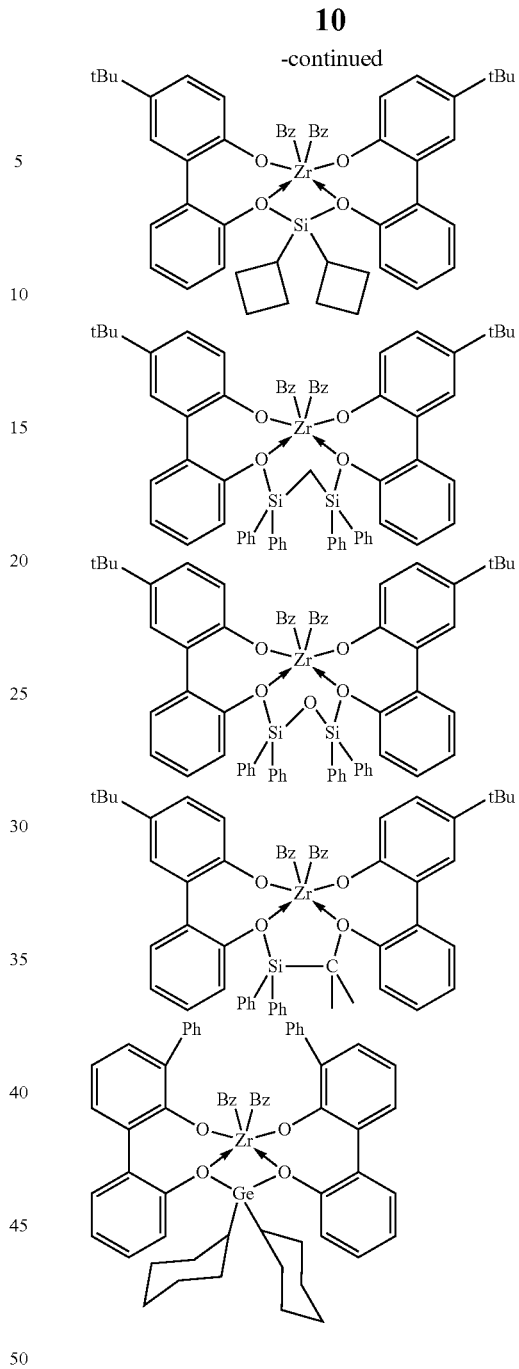

In a preferred embodiment in any of the processes described herein, one catalyst compound is used, e.g., the catalyst compounds are not different. For purposes of this invention, one catalyst compound is considered different from another if they differ by at least one atom. For example, "1,2-bis(2'-phenyl,3-biphenyl)dimethylsilyl titanium dibromide" is different from "1,2-bis(2'-phenyl,3-biphenyl)dimethylsilyl zirconium dibromide" Catalyst compounds that differ only by isomer are considered the same for purposes of this invention.

In some embodiments, two or more different catalyst compounds are present in the catalyst system used herein. In some embodiments, two or more different catalyst compounds are present in the reaction zone where the process(es) described herein occur. When two transition metal compound based catalysts are used in one reactor as a mixed catalyst system, the two transition metal compounds are preferably chosen such that the two are compatible. A simple screening method such as by $^1$H or $^{13}$C NMR, known to those of ordinary skill in the art, can be used to determine which transition metal compounds are compatible. It is preferable to use the same activator for the transition metal compounds, however, two different activators, such as a non-coordinating anion activator and an alumoxane, can be used in combination. If one or more transition metal compounds contain an X ligand which is not a hydride, hydrocarbyl, or substituted hydrocarbyl, then the alumoxane may be contacted with the transition metal compounds prior to addition of the non-coordinating anion activator.

The two transition metal compounds (pre-catalysts) may be used in any ratio. Preferred molar ratios of (A) transition metal compound to (B) transition metal compound fall within the range of (A:B) 1:1000 to 1000:1, alternatively 1:100 to 500:1, alternatively 1:10 to 200:1, alternatively 1:1 to 100:1, alternatively 1:1 to 75:1, and alternatively 5:1 to 50:1. The particular ratio chosen will depend on the exact pre-catalysts chosen, the method of activation, and the end product desired. In a particular embodiment, when using the two pre-catalysts, where both are activated with the same activator, useful mole percents, based upon the molecular weight of the pre-catalysts, are 10 to 99.9% A to 0.1 to 90% B, alternatively 25 to 99% A to 0.5 to 50% B, alternatively 50 to 99% A to 1 to 25% B, and alternatively 75 to 99% A to 1 to 10% B.

Methods to Prepare the Catalyst Compounds

Catalyst compounds described herein can be prepared by the general pathway shown below (where M and X are as defined above, x is a number from 1 to 12, e.g., 0, 1, 2, 3, 4, 5, 6, 7, 8, 9, 10, 11, or 12, and THP is tetrahydropyran):

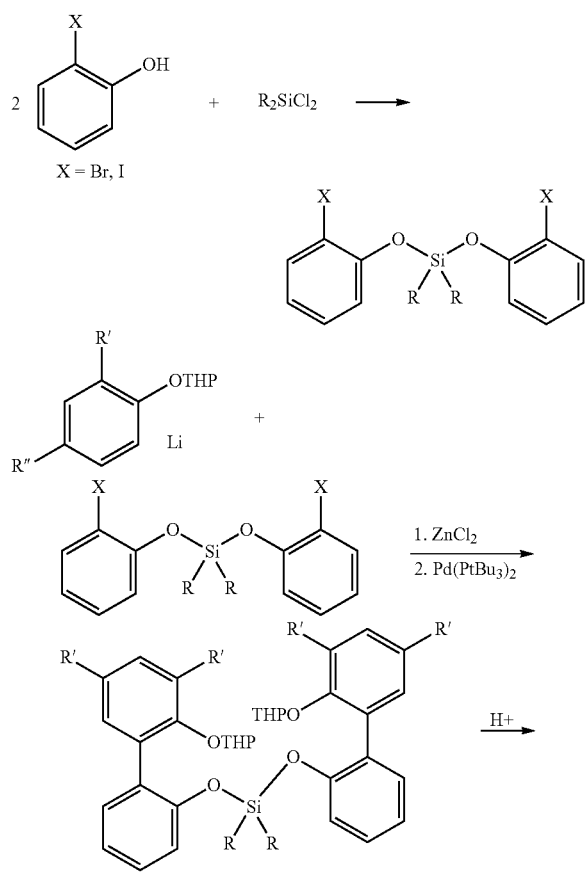

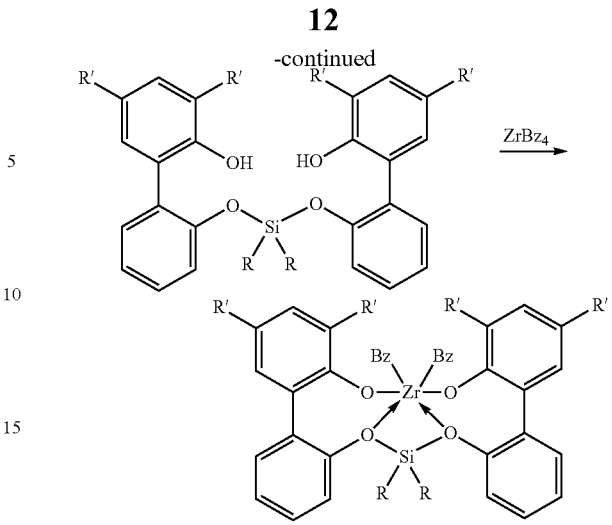

Activators

The terms "cocatalyst" and "activator" are used herein interchangeably and are defined to be any compound which can activate any one of the catalyst compounds described above by converting the neutral catalyst compound to a catalytically active catalyst compound cation.

After the complexes described above have been synthesized, catalyst systems may be formed by combining them with activators in any manner known from the literature including by supporting them for use in slurry or gas phase polymerization. The catalyst systems may also be added to or generated in solution polymerization or bulk polymerization (in the monomer). The catalyst system typically comprises a complex as described above and an activator such as alumoxane or a non-coordinating anion.

Non-limiting activators, for example, include alumoxanes, aluminum alkyls, ionizing activators, which may be neutral or ionic, and conventional-type cocatalysts. Preferred activators typically include alumoxane compounds, modified alumoxane compounds, and ionizing anion precursor compounds that abstract a reactive, σ-bound, metal ligand making the metal complex cationic and providing a charge-balancing noncoordinating or weakly coordinating anion.

Alumoxane Activators

In one embodiment, alumoxane activators are utilized as an activator in the catalyst system. Alumoxanes are generally oligomeric compounds containing —Al(R*)—O— subunits, where R* is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is an alkyl, halide, alkoxide or amide. Mixtures of different alumoxanes and modified alumoxanes may also be used. It may be preferable to use a visually clear methylalumoxane. A cloudy or gelled alumoxane can be filtered to produce a clear solution or clear alumoxane can be decanted from the cloudy solution. A useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

When the activator is an alumoxane (modified or unmodified), some embodiments select the maximum amount of activator typically at up to a 5000-fold molar excess Al/M over the catalyst compound (per metal catalytic site). The minimum activator-to-catalyst-compound is a 1:1 molar ratio. Alternate preferred ranges include from 1:1 to 500:1, alternately from 1:1 to 200:1, alternately from 1:1 to 100:1, or alternately from 1:1 to 50:1.

In an alternate embodiment, little or no alumoxane is used in the polymerization processes described herein. Preferably, alumoxane is present at zero mole %, alternately the alumoxane is present at a molar ratio of aluminum to catalyst compound transition metal less than 500:1, preferably less than 300:1, preferably less than 100:1, preferably less than 1:1.

Non-Coordinating Anion Activators

A non-coordinating anion (NCA) is defined to mean an anion either that does not coordinate to the catalyst metal cation or that does coordinate to the metal cation, but only weakly. The term NCA is also defined to include multicomponent NCA-containing activators, such as N,N-dimethylanilinium tetrakis(pentafluorophenyl)borate, that contain an acidic cationic group and the non-coordinating anion. The term NCA is also defined to include neutral Lewis acids, such as tris(pentafluorophenyl)boron, that can react with a catalyst to form an activated species by abstraction of an anionic group. An NCA coordinates weakly enough that a neutral Lewis base, such as an olefinically or acetylenically unsaturated monomer can displace it from the catalyst center. Any metal or metalloid that can form a compatible, weakly coordinating complex may be used or contained in the noncoordinating anion. Suitable metals include, but are not limited to, aluminum, gold, and platinum. Suitable metalloids include, but are not limited to, boron, aluminum, phosphorus, and silicon. A stoichiometric activator can be either neutral or ionic. The terms ionic activator, and stoichiometric ionic activator can be used interchangeably. Likewise, the terms neutral stoichiometric activator, and Lewis acid activator can be used interchangeably. The term non-coordinating anion includes neutral stoichiometric activators, ionic stoichiometric activators, ionic activators, and Lewis acid activators.

"Compatible" non-coordinating anions are those which are not degraded to neutrality when the initially formed complex decomposes. Further, the anion will not transfer an anionic substituent or fragment to the cation so as to cause it to form a neutral transition metal compound and a neutral by-product from the anion. Non-coordinating anions useful in accordance with this invention are those that are compatible, stabilize the transition metal cation in the sense of balancing its ionic charge at +1, and yet retain sufficient lability to permit displacement during polymerization.

It is within the scope of this invention to use an ionizing or stoichiometric activator, neutral or ionic, such as tri (n-butyl) ammonium tetrakis (pentafluorophenyl) borate, a tris perfluorophenyl boron metalloid precursor or a tris perfluoronaphthyl boron metalloid precursor, polyhalogenated heteroborane anions (WO 98/43983), boric acid (U.S. Pat. No. 5,942,459), or combination thereof. It is also within the scope of this invention to use neutral or ionic activators alone or in combination with alumoxane or modified alumoxane activators.

The catalyst systems of this invention can include at least one non-coordinating anion (NCA) activator.

In a preferred embodiment, boron-containing NCA activators represented by the formula below can be used:

where: Z is (L-H) or a reducible Lewis acid; L is a neutral Lewis base; H is hydrogen; (L-H) is a Bronsted acid; $A^{d-}$ is a boron-containing, non-coordinating anion having the charge d− and/or d is 1, 2, or 3.

The cation component, $Z_d^+$ may include Bronsted acids such as protons or protonated Lewis bases or reducible Lewis acids capable of protonating or abstracting a moiety, such as an alkyl or aryl, from the transition metal catalyst precursor, resulting in a cationic transition metal species.

The activating cation $Z_d^+$ may also be a moiety such as silver, tropylium, carboniums, ferroceniums, and mixtures, preferably carboniums and ferroceniums. Most preferably $Z_d^+$ is triphenyl carbonium. Preferred reducible Lewis acids can be any triaryl carbonium (where the aryl can be substituted or unsubstituted, such as those represented by the formula: $(Ar_3C^+)$, where Ar is aryl or aryl substituted with a heteroatom, a $C_1$ to $C_{40}$ hydrocarbyl, or a substituted $C_1$ to $C_{40}$ hydrocarbyl), preferably the reducible Lewis acids in formula above as "Z" include those represented by the formula: $(Ph_3C)$, where Ph is a substituted or unsubstituted phenyl, preferably substituted with one or more $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics, preferably Z is a triphenylcarbonium.

When $Z_d^+$ is the activating cation $(L-H)_d^+$, it is preferably a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxomiums from ethers such as dimethyl ether, diethyl ether, tetrahydrofuran and dioxane, sulfoniums from thioethers, such as diethyl thioethers, tetrahydrothiophene, and mixtures thereof.

The anion component $A^{d-}$ includes those having the formula $[M^{k+}Q_n]^{d-}$ wherein k is 1, 2, or 3; n is 1, 2, 3, 4, 5, or 6 (preferably 1, 2, 3, or 4); n−k=d; M is an element selected from Group 13 of the Periodic Table of the Elements, preferably boron or aluminum, and Q is, independently, a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ also include diboron compounds as disclosed in U.S. Pat. No. 5,447,895, which is fully incorporated herein by reference.

Illustrative, but not limiting examples of boron compounds which may be used as an activating cocatalyst are the compounds described as (and particularly those specifically listed as) activators in U.S. Pat. No. 8,658,556, which is incorporated by reference herein.

Most preferably, the ionic stoichiometric activator $Z_d^+$ ($A^{d-}$) is one or more of N,N-dimethylanilinium tetra(perfluorophenyl)borate, N,N-dimethylanilinium tetrakis(perfluoronaphthyl)borate, N,N-dimethylanilinium tetrakis(perfluoro-biphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis-(perfluorobiphenyl)borate, triphenylcarbenium tetrakis (3,5-bis(trifluoromethyl)-phenyl)borate, or triphenylcarbenium tetra(perfluorophenyl)borate.

Bulky activators are also useful herein as NCAs. "Bulky activator" as used herein refers to anionic activators represented by the formula:

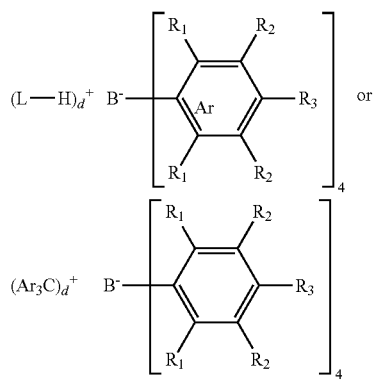

where:
each $R_1$ is, independently, a halide, preferably a fluoride;
Ar is substituted or unsubstituted aryl group (preferably a substituted or unsubstituted phenyl), preferably substituted with $C_1$ to $C_{40}$ hydrocarbyls, preferably $C_1$ to $C_{20}$ alkyls or aromatics;
each $R_2$ is, independently, a halide, a $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—Si—$R_a$, where $R_a$ is a $C_1$ to $C_{20}$ hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); and
L is an neutral Lewis base; (L-H)$^+$ is a Bronsted acid; d is 1, 2, or 3;
wherein the anion has a molecular weight of greater than 1020 g/mol; and
at least three of the substituents on the B atom each have a molecular volume of greater than 250 cubic Å, alternately greater than 300 cubic Å, or alternately greater than 500 cubic Å.

Preferably $(Ar_3C)_d^+$ is $(Ph_3C)_d^+$, where Ph is a substituted or unsubstituted phenyl, preferably substituted with $C_1$ to $C_{40}$ hydrocarbyls or substituted $C_1$ to $C_{40}$ hydrocarbyls, preferably $C_1$ to $C_{20}$ alkyls or aromatics or substituted $C_1$ to $C_{20}$ alkyls or aromatics.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

Molecular volume may be calculated as reported in "A Simple "Back of the Envelope" Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: $MV=8.3V_s$, where $V_s$ is the scaled volume. $V_s$ is the sum of the relative volumes of the constituent atoms, and is calculated from the molecular formula of the substituent using the following table of relative volumes. For fused rings, the $V_s$ is decreased by 7.5% per fused ring.

| Element | Relative Volume |
| --- | --- |
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

For a list of particularly useful Bulky activators please see U.S. Pat. No. 8,658,556, which is incorporated by reference herein.

In another embodiment, one or more of the NCA activators is chosen from the activators described in U.S. Pat. No. 6,211,105.

Preferred activators include N,N-dimethylanilinium tetrakis(perfluoro-naphthyl)borate, N,N-dimethylanilinium tetrakis(perfluorobiphenyl)-borate, N,N-dimethylanilinium tetrakis(perfluorophenyl)borate, N,N-dimethylanilinium tetrakis(3,5-bis(trifluoromethyl)phenyl)borate, triphenylcarbenium tetrakis(perfluoro-naphthyl)borate, triphenylcarbenium tetrakis(perfluorobiphenyl)borate, triphenyl-carbenium tetrakis(3,5-bis(trifluoromethyl)phenyl)borate, triphenylcarbenium tetrakis-(perfluorophenyl)borate, [Ph$_3$C$^+$][B(C$_6$F$_5$)$_4^-$], [Me$_3$NH$^+$][B(C$_6$F$_5$)$_4^-$], 1-(4-(tris(penta-fluorophenyl)borate)-2,3,5,6-tetrafluorophenyl)pyrrolidinium, and tetrakis(pentafluoro-phenyl)borate, 4-(tris(pentafluorophenyl)borate)-2,3,5,6-tetrafluoropyridine.

In a preferred embodiment, the activator comprises a triaryl carbonium (such as triphenylcarbenium tetraphenylborate, triphenylcarbenium tetrakis(pentafluoro-phenyl)borate, triphenylcarbenium tetrakis-(2,3,4,6-tetrafluorophenyl) borate, triphenylcarbenium tetrakis(perfluoronaphthyl) borate, triphenylcarbenium tetrakis(per-fluorobiphenyl) borate, triphenylcarbenium tetrakis(3,5-bis(trifluoromethyl)-phenyl)borate).

In another embodiment, the activator comprises one or more of trialkylammonium tetrakis(pentafluorophenyl)borate, N,N-dialkylanilinium tetrakis(pentafluorophenyl)-borate, N,N-dimethyl-(2,4,6-trimethylanilinium) tetrakis(pentafluorophenyl)borate, trialkylammonium tetrakis-(2,3,4,6-tetrafluorophenyl) borate, N,N-dialkylanilinium tetrakis-(2,3,4,6-tetrafluorophenyl)borate, trialkylammonium tetrakis(perfluoronaphthyl)-borate, N,N-dialkylanilinium tetrakis(perfluoronaphthyl)borate, trialkylammonium tetrakis(perfluorobiphenyl)borate, N,N-dialkylanilinium (perfluorobiphenyl)-borate, trialkylammonium tetrakis(3,5-bis(trifluoromethyl)phenyl)borate, N,N-dialkylanilinium tetrakis(3,5-bis(trifluoromethyl)phenyl)borate, N,N-dialkyl-(2,4,6-trimethylanilinium) tetrakis(3,5-bis(trifluoromethyl)phenyl)borate, or di-(i-propyl)-ammonium tetrakis(pentafluorophenyl)borate (where alkyl is methyl, ethyl, propyl, n-butyl, sec-butyl, or t-butyl).

The typical activator-to-catalyst ratio, e.g., all NCA activators-to-catalyst ratio is about a 1:1 molar ratio. Alternate preferred ranges include from 0.1:1 to 100:1, alternately from 0.5:1 to 200:1, alternately from 1:1 to 500:1, alternately from 1:1 to 1000:1. A particularly useful range is from 0.5:1 to 10:1, preferably 1:1 to 5:1.

It is also within the scope of this invention that the catalyst compounds can be combined with combinations of alumoxanes and NCA's (see, for example, U.S. Pat. Nos. 5,153,157; 5,453,410; EP 0 573 120; WO 94/07928; and WO 95/14044, which discuss the use of an alumoxane in combination with an ionizing activator).

Chain Transfer Agents

Useful chain transfer agents are typically alkylalumoxanes, a compound represented by the formula $AlR_3$, $ZnR_2$ (where each R is, independently, a $C_1$-$C_8$ aliphatic radical, preferably methyl, ethyl, propyl, butyl, pentyl, hexyl, octyl, or an isomer thereof) or a combination thereof, such as diethyl zinc, methylalumoxane, trimethylaluminum, triisobutylaluminum, trioctylaluminum, or a combination thereof.

Optional Scavengers or Co-Activators

In addition to these activator compounds, scavengers or co-activators may be used. Aluminum alkyl or organoaluminum compounds, which may be utilized as scavengers or co-activators include, for example, trimethylaluminum, triethylaluminum, triisobutylaluminum, tri-n-hexylaluminum, tri-n-octylaluminum, and diethyl zinc.

Optional Support Materials

In embodiments herein, the catalyst system may comprise an inert support material. Preferably the supported material is a porous support material, for example, talc, and inorganic oxides. Other support materials include zeolites, clays, organoclays, or any other organic or inorganic support material and the like, or mixtures thereof.

Preferably, the support material is an inorganic oxide in a finely divided form. Suitable inorganic oxide materials for use in catalyst systems herein include Groups 2, 4, 13, and 14 metal oxides, such as silica, alumina, and mixtures thereof. Other inorganic oxides that may be employed either alone or in combination with the silica, or alumina are magnesia, titania, zirconia, and the like. Other suitable support materials, however, can be employed, for example, finely divided functionalized polyolefins, such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania, and the like. Preferred support materials include $Al_2O_3$, $ZrO_2$, $SiO_2$, and combinations thereof, more preferably $SiO_2$, $Al_2O_3$, or $SiO_2/Al_2O_3$.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 µm. More preferably, the surface area of the support material is in the range of from about 50 to about 500 $m^2/g$, pore volume of from about 0.5 to about 3.5 cc/g and average particle size of from about 10 to about 200 µm. Most preferably, the surface area of the support material is in the range from about 100 to about 400 $m^2/g$, pore volume from about 0.8 to about 3.0 cc/g, and average particle size is from about 5 to about 100 µm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 $m^2/gm$; pore volume of 1.65 $cm^3/gm$). Preferred silicas are marketed under the tradenames of DAVISON™ 952 or DAVISON™ 955 by the Davison Chemical Division of W.R. Grace and Company. In other embodiments, DAVISON™ 948 silica is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours. The calcined support material must have at least some reactive hydroxyl (OH) groups to produce supported catalyst systems of this invention. The calcined support material is then contacted with at least one polymerization catalyst comprising at least one catalyst compound and an activator.

The support material, having reactive surface groups, typically hydroxyl groups, is slurried in a non-polar solvent and the resulting slurry is contacted with a solution of a catalyst compound and an activator. In some embodiments, the slurry of the support material is first contacted with the activator for a period of time in the range of from about 0.5 hours to about 24 hours, from about 2 hours to about 16 hours, or from about 4 hours to about 8 hours. The solution of the catalyst compound is then contacted with the isolated support/activator. In some embodiments, the supported catalyst system is generated in situ. In an alternate embodiment, the slurry of the support material is first contacted with the catalyst compound for a period of time in the range of from about 0.5 hours to about 24 hours, from about 2 hours to about 16 hours, or from about 4 hours to about 8 hours. The slurry of the supported catalyst compound is then contacted with the activator solution.

The mixture of the catalyst, activator and support is heated to about 0° C. to about 70° C., preferably to about 23° C. to about 60° C., preferably at room temperature. Contact times typically range from about 0.5 hours to about 24 hours, from about 2 hours to about 16 hours, or from about 4 hours to about 8 hours.

Suitable non-polar solvents are materials in which all of the reactants used herein, i.e., the activator, and the catalyst compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene, and ethylbenzene, may also be employed.

Polymerization Processes

In embodiments herein, the invention relates to polymerization processes where monomer (such as propylene), and optionally comonomer, are contacted with a catalyst system comprising an activator and at least one catalyst compound, as described above. The catalyst compound and activator may be combined in any order, and are combined typically prior to contacting with the monomer.

Monomers useful herein include substituted or unsubstituted $C_2$ to $C_{40}$ alpha olefins, preferably $C_2$ to $C_{20}$ alpha olefins, preferably $C_2$ to $C_{12}$ alpha olefins, preferably ethylene, propylene, butene, pentene, hexene, heptene, octene, nonene, decene, undecene, dodecene, and isomers thereof. In a preferred embodiment of the invention, the monomer comprises propylene and optional comonomer(s) comprising one or more ethylene or $C_4$ to $C_{40}$ olefins, preferably $C_4$ to $C_{20}$ olefins, or preferably $C_6$ to $C_{12}$ olefins. The $C_4$ to $C_{40}$ olefin monomers may be linear, branched, or cyclic. The $C_4$ to $C_{40}$ cyclic olefins may be strained or unstrained, monocyclic or polycyclic, and may optionally include heteroatoms and/or one or more functional groups. In another preferred embodiment, the monomer comprises ethylene and optional comonomer(s) comprising one or more $C_3$ to $C_{40}$ olefins, preferably $C_4$ to $C_{20}$ olefins, or preferably $C_6$ to $C_{12}$ olefins. The $C_3$ to $C_{40}$ olefin monomers may be linear, branched, or cyclic. The $C_3$ to $C_{40}$ cyclic olefins may be strained or unstrained, monocyclic or polycyclic, and may optionally include heteroatoms and/or one or more functional groups.

Exemplary $C_2$ to $C_{40}$ olefin monomers and optional comonomers include ethylene, propylene, butene, pentene, hexene, heptene, octene, nonene, decene, undecene, dodecene, norbornene, norbornadiene, ethylidene norbornene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof, preferably hexene, heptene, octene, nonene, decene, dodecene, cyclooctene, 1,5-cyclooctadiene, 1-hydroxy-4-cyclooctene, 1-acetoxy-4-cyclooctene, 5-methylcyclopentene, cyclopentene, dicyclopentadiene, norbornene, norbornadiene, and their respective homologs and derivatives.

In a preferred embodiment, one or more dienes are present in the polymer produced herein at up to 10 wt %, preferably at 0.00001 to 1.0 wt %, preferably 0.002 to 0.5 wt %, even more preferably 0.003 to 0.2 wt %, based upon the total weight of the composition. In some embodiments, 500 ppm or less of diene is added to the polymerization, preferably 400 ppm or less, preferably 300 ppm or less. In other embodiments, at least 50 ppm of diene is added to the polymerization, or 100 ppm or more, or 150 ppm or more.

Preferred diolefin monomers useful in this invention include any hydrocarbon structure, preferably $C_4$ to $C_{30}$, having at least two unsaturated bonds, wherein at least two of the unsaturated bonds are readily incorporated into a polymer by either a stereospecific or a non-stereospecific catalyst(s). It is further preferred that the diolefin monomers be selected from alpha, omega-diene monomers (i.e., divinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene, or higher ring-containing diolefins with or without substituents at various ring positions.

Polymerization processes of this invention can be carried out in any manner known in the art. Any suspension, homogeneous, bulk, solution, slurry, or gas phase polymerization process known in the art can be used. Such processes can be run in a batch, semi-batch, or continuous mode. Homogeneous polymerization processes and slurry processes are preferred. (A homogeneous polymerization process is defined to be a process where at least 90 wt % of the product is soluble in the reaction media.) A bulk homogeneous process is particularly preferred. (A bulk process is defined to be a process where monomer concentration in all feeds to the reactor is 70 vol % or more.) Alternately, no solvent or diluent is present or added in the reaction medium, (except for the small amounts used as the carrier for the catalyst system or other additives; or amounts typically found with the monomer; e.g., propane in propylene). In another embodiment, the process is a slurry process. As used herein, the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

Suitable diluents/solvents for polymerization include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof, such as can be found commercially (Isopar™); perhalogenated hydrocarbons, such as perfluorinated $C_{4-10}$ alkanes, chlorobenzene, and aromatic and alkylsubstituted aromatic compounds, such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, 1-decene, and mixtures thereof. In a preferred embodiment, aliphatic hydrocarbon solvents are used as the solvent, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably less than 0.5 wt %, preferably less than 0 wt % based upon the weight of the solvents.

In a preferred embodiment, the feed concentration of the monomers and comonomers for the polymerization is 60 vol % solvent or less, preferably 40 vol % or less, or preferably 20 vol % or less, based on the total volume of the feedstream. Preferably the polymerization is run in a bulk process.

Preferred polymerizations can be run at any temperature and/or pressure suitable to obtain the desired ethylene polymers. Typical temperatures and/or pressures include a temperature in the range of from about 0° C. to about 300° C., preferably about 20° C. to about 200° C., preferably about 35° C. to about 150° C., preferably from about 40° C. to about 120° C., preferably from about 45° C. to about 80° C.; and at a pressure in the range of from about 0.35 MPa to about 10 MPa, preferably from about 0.45 MPa to about 6 MPa, or preferably from about 0.5 MPa to about 4 MPa.

In a typical polymerization, the run time of the reaction is up to 300 minutes, preferably in the range of from about 5 to 250 minutes, or preferably from about 10 to 120 minutes.

In a some embodiments, hydrogen is present in the polymerization reactor at a partial pressure of 0.001 to 50 psig (0.007 to 345 kPa), preferably from 0.01 to 25 psig (0.07 to 172 kPa), more preferably 0.1 to 10 psig (0.7 to 70 kPa).

In a preferred embodiment, little or no alumoxane is used in the process to produce the polymers. Preferably, alumoxane is present at zero mol %, alternately the alumoxane is present at a molar ratio of aluminum to transition metal less than 500:1, preferably less than 300:1, preferably less than 100:1, preferably less than 1:1.

In a preferred embodiment, little or no scavenger is used in the process to produce the ethylene polymer. Preferably, scavenger (such as trialkyl aluminum) is present at zero mol %, alternately the scavenger is present at a molar ratio of scavenger metal to transition metal of less than 100:1, preferably less than 50:1, preferably less than 15:1, preferably less than 10:1.

In a preferred embodiment, the polymerization: 1) is conducted at temperatures of 0 to 300° C. (preferably 25 to 150° C., preferably 40 to 120° C., preferably 45 to 80° C.); 2) is conducted at a pressure of atmospheric pressure to 10 MPa (preferably 0.35 to 10 MPa, preferably from 0.45 to 6 MPa, preferably from 0.5 to 4 MPa); 3) is conducted in an aliphatic hydrocarbon solvent (such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof; preferably where aromatics are preferably present in the solvent at less than 1 wt %, preferably less than 0.5 wt %, preferably at 0 wt % based upon the weight of the solvents); 4) wherein the catalyst system used in the polymerization comprises less than 0.5 mol %, preferably 0 mol % alumoxane, alternately the alumoxane is present at a molar ratio of aluminum to transition metal less than 500:1, preferably less than 300:1, preferably less than 100:1, preferably less than 1:1; 5) the polymerization preferably occurs in one reaction zone; 6) the productivity of the catalyst compound is at least 80,000 g/mmol/hr (preferably at least 150,000 g/mmol/hr, preferably at least 200,000 g/mmol/hr, preferably at least 250,000 g/mmol/hr, preferably at least 300,000 g/mmol/hr); 7) optionally scavengers (such as trialkyl aluminum compounds) are absent (e.g., present at zero mol %, alternately the scavenger is present at a molar ratio of scavenger metal to transition metal of less than 100:1, preferably less than 50:1, preferably less than 15:1, preferably less than 10:1); and 8) optionally hydrogen is present in the polymerization reactor at a partial pressure of 0.001 to 50 psig (0.007 to 345 kPa) (preferably from 0.01 to 25 psig (0.07 to 172 kPa), more preferably 0.1 to 10 psig (0.7 to 70 kPa)). In a preferred embodiment, the catalyst system used in the polymerization comprises no more than one catalyst compound. A "reaction zone" also referred to as a "polymerization zone" is a vessel where polymerization takes place, for example, a batch reactor. When multiple reactors are used in either series or parallel configuration, each reactor is considered as a separate polymerization zone. For a multi-stage polymerization in both a batch reactor and a continuous reactor, each polymerization stage is considered as a separate polymerization zone. In a preferred embodiment, the polymerization occurs in one reaction zone.

Other additives may also be used in the polymerization, as desired, such as one or more scavengers, promoters, modifiers, chain transfer agents (useful chain transfer agents are described above), reducing agents, oxidizing agents, hydrogen, aluminum alkyls, or silanes.

Polyolefin Products

This invention also relates to compositions of matter produced by the methods described herein.

In a preferred embodiment, the process described herein produces ethylene homopolymers or ethylene copolymers, such as ethylene-propylene and/or ethylene-alphaolefin (preferably $C_3$ to $C_{20}$) copolymers (such as ethpylene-hexene copolymers or ethpylene-octene copolymers) having: a Mw/Mn of greater than 1 to 4 (preferably greater than 1 to 3).

Likewise, the process of this invention produces olefin polymers, preferably polyethylene and polypropylene homopolymers and copolymers. In a preferred embodiment, the polymers produced herein are homopolymers of ethylene or propylene, are copolymers of ethylene preferably having from 0 to 25 mol % (alternately from 0.5 to 20 mol %, alternately from 1 to 15 mol %, preferably from 3 to 10 mol %) of one or more $C_3$ to $C_{20}$ olefin comonomer (preferably $C_3$ to $C_{12}$ alpha-olefin; preferably propylene, butene, hexene, octene, decene, dodecene; preferably propylene, butene, hexene, octene, and/or cyclic olefins such as norbornene, vinyl norbornene), or are copolymers of propylene preferably having from 0 to 25 mol % (alternately from 0.5 to 20 mol %, alternately from 1 to 15 mol %, preferably from 3 to 10 mol %) of one or more of $C_2$ or $C_4$ to $C_{20}$ olefin comonomer (preferably ethylene or $C_4$ to $C_{12}$ alpha-olefin; preferably ethylene, butene, hexene, octene, decene, dodecene; preferably ethylene, butene, hexene, octene, norbornene, vinyl norbornene, ethylidene norbornene).

In a preferred embodiment, the monomer is ethylene and the comonomer is hexene, preferably from 1 to 15 mol % hexene, alternately 1 to 10 mol %.

In a preferred embodiment, the polymer comprises cyclic comonomers. In a preferred embodiment, the copolymer comprises comonomers of norbornene, vinyl norbornene, and/or ethylidene norbornene.

Typically, the polymers produced herein have an Mw of 100 to 50,000 g/mol (preferably 150 to 25,000 g/mol, preferably 200 to 10,000 g/mol, preferably 250 to 5,000 g/mol, preferably 250 to 1,000 g/mol), and/or an Mw/Mn of greater than 1 to 40 (alternately 1.2 to 20, alternately 1.3 to 10, alternately 1.4 to 5, 1.5 to 4, alternately 1.5 to 3).

In a preferred embodiment, the polymer produced herein has a unimodal or multimodal molecular weight distribution as determined by Gel Permeation Chromotography (GPC). By "unimodal" is meant that the GPC trace has one peak or inflection point. By "multimodal" is meant that the GPC trace has at least two peaks or inflection points. An inflection point is that point where the second derivative of the curve changes in sign (e.g., from negative to positive or vice versa).

Unless otherwise indicated Mw, Mn, MWD are determined by GPC as described in US 2006/0173123 page 24-25, paragraphs [0334] to [0341].

In a preferred embodiment, the polymer produced herein has a composition distribution breadth index (CDBI) of 50% or more, preferably 60% or more, preferably 70% or more. CDBI is a measure of the composition distribution of monomer within the polymer chains and is measured by the procedure described in PCT publication WO 93/03093, published Feb. 18, 1993, specifically columns 7 and 8, as well as in Wild et al., J. Poly. Sci., Poly. Phys. Ed., Vol. 20, p. 441 (1982) and U.S. Pat. No. 5,008,204, including that fractions having a weight average molecular weight (Mw) below 15,000 are ignored when determining CDBI.

Blends

In another embodiment, the polymer (preferably the polyethylene or polypropylene) produced herein is combined with one or more additional polymers prior to being formed into a film, molded part or other article. Other useful polymers include polyethylene, isotactic polypropylene, highly isotactic polypropylene, syndiotactic polypropylene, random copolymer of propylene and ethylene, and/or butene, and/or hexene, polybutene, ethylene vinyl acetate, LDPE, LLDPE, HDPE, ethylene vinyl acetate, ethylene methyl acrylate, copolymers of acrylic acid, polymethylmethacrylate, or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, cross linked polyethylene, copolymers of ethylene and vinyl alcohol (EVOH), polymers of aromatic monomers such as polystyrene, poly-1 esters, polyacetal, polyvinylidine fluoride, polyethylene glycols, and/or polyisobutylene.

In a preferred embodiment, the polymer (preferably the polyethylene or polypropylene) is present in the above blends, at from 10 to 99 wt %, based upon the weight of the polymers in the blend, preferably 20 to 95 wt %, even more preferably at least 30 to 90 wt %, even more preferably at least 40 to 90 wt %, even more preferably at least 50 to 90 wt %, even more preferably at least 60 to 90 wt %, even more preferably at least 70 to 90 wt %.

The blends described above may be produced by mixing the polymers of the invention with one or more polymers (as described above), by connecting reactors together in series to make reactor blends or by using more than one catalyst in the same reactor to produce multiple species of polymer. The polymers can be mixed together prior to being put into the extruder or may be mixed in an extruder.

The blends may be formed using conventional equipment and methods, such as by dry blending the individual components and subsequently melt mixing in a mixer, or by mixing the components together directly in a mixer, such as, for example, a Banbury mixer, a Haake mixer, a Brabender internal mixer, or a single or twin-screw extruder, which may include a compounding extruder and a side-arm extruder used directly downstream of a polymerization process, which may include blending powders or pellets of the resins at the hopper of the film extruder. Additionally, additives may be included in the blend, in one or more components of the blend, and/or in a product formed from the blend, such as a film, as desired. Such additives are well known in the art, and can include, for example: fillers; antioxidants (e.g., hindered phenolics such as IRGANOX™ 1010 or IRGANOX™ 1076 available from Ciba-Geigy); phosphites (e.g., IRGAFOS™ 168 available from Ciba-Geigy); anti-cling additives; tackifiers, such as polybutenes, terpene resins, aliphatic and aromatic hydrocarbon resins, alkali metal and glycerol stearates, and hydrogenated rosins; UV stabilizers; heat stabilizers; anti-blocking agents; release agents; anti-static agents; pigments; colorants; dyes; waxes; silica; fillers; talc; and the like.

Films

Specifically, any of the foregoing polymers, such as the foregoing polypropylenes or blends thereof, may be used in a variety of end-use applications. Such applications include, for example, mono- or multi-layer blown, extruded, and/or shrink films. These films may be formed by any number of well known extrusion or coextrusion techniques, such as a blown bubble film processing technique, wherein the composition can be extruded in a molten state through an annular die and then expanded to form a uniaxial or biaxial orientation melt prior to being cooled to form a tubular, blown film, which can then be axially slit and unfolded to form a flat film. Films may be subsequently unoriented, uniaxially oriented, or biaxially oriented to the same or different extents. One or more of the layers of the film may be oriented in the transverse and/or longitudinal directions to the same or different extents. The uniaxially orientation can be accomplished using typical cold drawing or hot drawing methods. Biaxial orientation can be accomplished using tenter frame equipment or double bubble processes and may occur before or after the individual layers are brought together. For example, a polyethylene layer can be extrusion coated or laminated onto an oriented polypropylene layer or the polyethylene and polypropylene can be coextruded together into a film then oriented. Likewise, oriented polypropylene could be laminated to oriented polyethylene or oriented polyethylene could be coated onto polypropylene then, optionally, the combination could be oriented even further. Typically the films are oriented in the Machine Direction (MD) at a ratio of up to 15, preferably between 5 and 7, and in the Transverse Direction (TD) at a ratio of up to 15, preferably 7 to 9. However, in another embodiment the film is oriented to the same extent in both the MD and TD directions.

The films may vary in thickness depending on the intended application; however, films of a thickness from 1 to 50 μm are usually suitable. Films intended for packaging are usually from 10 to 50 μm thick. The thickness of the sealing layer is typically 0.2 to 50 μm. There may be a sealing layer on both the inner and outer surfaces of the film or the sealing layer may be present on only the inner or the outer surface.

In another embodiment, one or more layers may be modified by corona treatment, electron beam irradiation, gamma irradiation, flame treatment, or microwave. In a preferred embodiment, one or both of the surface layers is modified by corona treatment.

Experimental

Materials and abbreviations used herein include:

RT is room temperature and is 23° C. unless otherwise indicated.

Dimethylanilinium tetrakisperfluorophenylborate (Activator 1) was obtained from Albemarle Corporation, Baton Rouge, La.

Compound A is

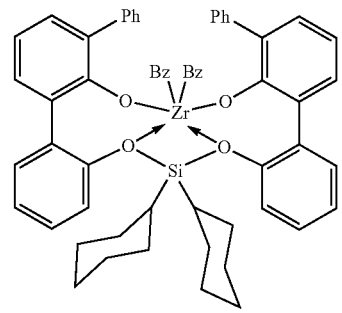

Catalyst compound A (inventive) is sysnthesized as follows:

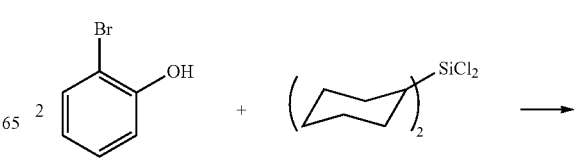

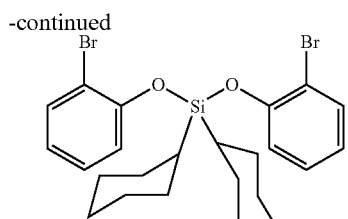

1

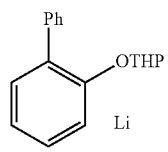

2

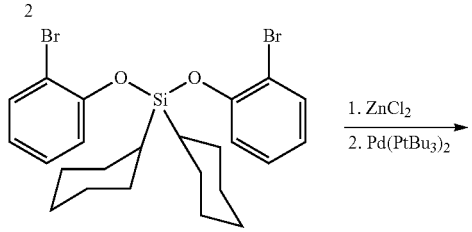

1. ZnCl$_2$
2. Pd(PtBu$_3$)$_2$

1

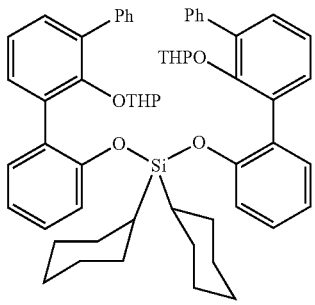

3

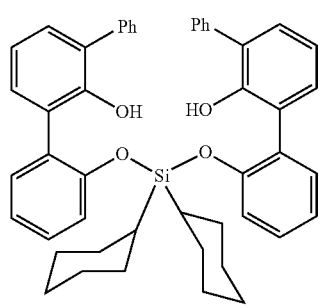

ZrBz$_4$

4

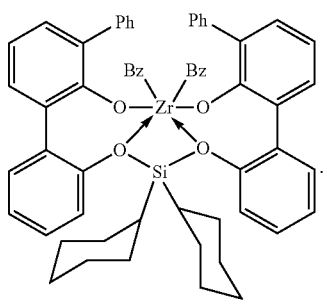

2-Bromophenol (7.8 g) and dicylohexyldichlorosilane (5.8 g) were dissolved in THF (100 mL). Slowly, KH (1.8 g) was added to the reaction mixture. After the addition, the reaction was heated to 60° C. for 1 hr. The reaction was cooled and volatiles removed. The white solid was recrystallized from hot toluene to yield pure 1 (5.6 g). Biphenylphenol (10 g) was dissolved in CH$_2$Cl$_2$ (60 mL) and reacted with para-toluenesulphonic acid (300 mg) followed by 2,3-dihydropyran (12 g). After 2 minutes, KOtBu (1.2 g) was added and the volatiles were removed. The crude was extracted with hexane (3×40 mL) and extracts were reduced to a viscous light yellow liquid (15.9 g). All was dissolved in Et$_2$O (80 mL) and reacted with nBuLi (17 g, 2.8 M). After 1 hr the white solid product (2) was filtered and washed with hexane (17.8 g). Complex 2 (4.4 g) was slurried in THF (60 mL) and reacted with ZnCl$_2$ (1.8 g). Complex 1 (3.1 g) was added followed by Pd(PtBu$_3$)$_2$ (80 mg) and the reaction mixture was heated to 80° C. for 4 hr. The crude reaction was reacted with 60 mL aqueous HCl (35%) for 2 hr. The reaction was extracted with Et$_2$O (2×60 mL) and dried with MgSO$_4$. The volatiles were removed to yield liquid product 4 (3.1 g). Complex 4 (1.3 g) was reacted with ZrBz$_4$ (0.8 g) in toluene (40 mL) at 80° C. for 3 hrs. The reaction was cooled to RT and hexane (20 mL) was added. The reaction was cooled to −30° C. The inventive complex was isolated as an off-white solid (0.65 g). $^1$H NMR (400 MHz, CD$_2$Cl$_2$) ppm; 7.6 to 6.1 (m, 34H), 2.18 (s, 4H), 1.88 to 0.10 (m, 22H).

The inventive complex was screened in a high throughput solution polymerization system and compared to an "O$_4$" complex containing carbon linkages (Catalyst B, comparative). The structure of Catalsyt B is shown below:

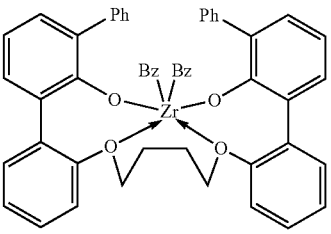

High Throughput Solution Polymerization—General Details

Typical solution polymerizations were carried out using high throughput robotic system manufactured by Symyx Technologies (Santa Clara, Calif.). The experimental details were developed using Library Studio version 7.1.9. The reactions were carried out in parallel with robotic control and typically took less than 2 hours for completion. Individual reaction wells were lined with disposable glass inserts and were equipped with Teflon stirring paddles. Stock solutions of complex and activator, dimethylanilinium tetrakisperfluorophenylborate, in toluene were added separately to an isohexane reaction solvent containing a specific amount of scavenger, Al(C$_8$H$_{17}$)$_3$. Monomers were then added and the reactions controlled either by time or in some cases by a pre-specified pressure drop. The total volume of monomers, solvent, pre-catalyst, activator and scavenger was maintained at 5.1 ml. The reactions were quenched with CO$_2$ addition and the volatiles were removed under reduced pressure at 70° C.

Inventive and comparative catalysts were screened in solution ethylene and propylene. The temperature was 80° C. and the amount of propylene in each run was 1.0 mL. The amount of catalyst was 0.02 micromole, the amount of activator was 0.02 micromole and the amount of Al(C$_8$H$_{17}$)$_3$ was 0.6 micromole used per cell. The results are shown in the Table below (average of duplicate runs) and show the large difference in molecular weight while maintaining activities and propylene incorporation.

| | ethylene (psi) | 75 | 100 | 125 |
|---|---|---|---|---|
| Catalyst A | $M_n$ (g/mol) | 307 | 292 | 318 |
| | Activity, (mg/s) | 2.1 | 3.6 | 7.4 |
| | propylene incorp, (wt %) | 59.5 | 51 | 58.6 |
| Catalyst B | $M_n$ (g/mol) | 390914 | 371905 | 479842 |
| | Activity, (mg/s) | 1.8 | 2.2 | 2.9 |
| | propylene incorp, (wt %) | 52.6 | 57.4 | 57.2 |

The inventive and comparative catalysts were screened with ethylene and octene at 80° C. using a constant ethylene partial pressure of 125 psi. The reactions were quenched at 20 psi ethylene uptake. The amount of catalyst was 0.02 micromole, the amount of activator was 0.02 micromole and the amount of $Al(C_8H_{17})_3$ was 0.6 micromole used per cell. The results are shown below (average of duplicate runs). The inventive catalysts show very low Mn and have better incorporation of octene.

| | Octene, microliter | 75 | 150 | 300 |
|---|---|---|---|---|
| Catalyst A | $M_n$ (g/mol) | 342 | 355 | 373 |
| | Activity, (mg/s) | 0.3 | 0.25 | 0.26 |
| | Octene incorp (wt %) | 17.3 | 20 | 26.9 |
| Catalyst B | $M_n$ (g/mol) | 500,061 | 578,552 | 628,176 |
| | Activity, (mg/s) | 1.1 | 1.3 | 1.61 |
| | Octene incorp, (wt %) | 7 | 12.2 | 20.6 |

The inventive and comparative catalysts were screened with ethylene and various levels of norbornene at 80° C. using a constant ethylene partial pressure of 125 psi. The reactions were quenched at 20 psi ethylene uptake. The amount of catalyst was 0.02 micromole, the amount of activator was 0.02 micromole and the amount of $Al(C_8H_{17})_3$ was 0.6 micromole used per cell. The results are shown below (average of duplicate runs). The inventive catalysts again show very low Mn and have better incorporation of norbornene. In addition, activities at all levels of norbornene are higher with the inventive catalyst A.

| | Norbornene, microliters | 100 | 250 | 400 |
|---|---|---|---|---|
| Catalyst A | $M_n$ (g/mol) | 444 | 533 | 702 |
| | Activity, (mg/s) | 3.2 | 3.4 | 1.9 |
| | Norbornene incorp, (mol %) | 31.7 | 41.2 | 47.6 |
| Catalyst B | $M_n$ (g/mol) | 684,533 | 876,544 | 723,509 |
| | Activity, (mg/s) | 1.4 | 0.5 | 0.13 |
| | Norbornene incorp, (mol %) | 9 | 14.3 | 21.7 |

Test Methods
[1]NMR

Mn ($^1$H NMR) was determined according to the following NMR method. $^1$H NMR data ws collected at either room temperature or 120° C. (for purposes of the claims, 120° C. shall be used) in a 5 mm probe using a Varian spectrometer with a $^1$H frequency of 400 MHz (for the purpose of the claims, a proton frequency of 400 MHz is used). Data were recorded using a maximum pulse width of 45° C., 8 seconds between pulses and signal averaging 120 transients. Spectral signals were integrated and the number of unsaturation types per 1000 carbons was calculated by multiplying the different groups by 1000 and dividing the result by the total number of carbons. Mn is calculated by dividing the total number of unsaturated species into 14,000, and has units of g/mol.

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise, whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

What is claimed is:

1. A catalyst compound represented by the formula:

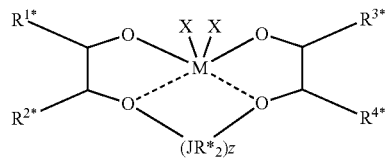

wherein
the dotted line indicates a dative bond;
M is a group 4 metal;
each J is, independently, Si or Ge, provided that when z is 2 or more, one $JR*_2$ group may be $CR*_2$;
z is a number from 1 to 12, provided that when z is 2, the two $JR*_2$ groups may be connected by a heteroatom, X*, to form a group represented by the formula $R*_2J$-$X*$-$JR*_2$;
each of $R^{1*}$, $R^{2*}$, $R^{3*}$, $R^{4*}$, and $R*$ is, independently, hydrogen, a substituted $C_1$ to $C_{40}$ hydrocarbyl group, a $C_2$ to $C_{40}$ unsubstituted hydrocarbyl group, or a heteroatom, provided that any adjacent R* groups may form a fused ring or multicenter fused ring system where the rings may be aromatic, partially saturated or saturated; and
each X is, independently, a substituted $C_1$ to $C_{40}$ hydrocarbyl group, a $C_1$ to $C_{40}$ unsubstituted hydrocarbyl group, a hydride, an amide, an alkoxide, a sulfide, a phosphide, a halide, an amine, a phosphine, an ether, a combination thereof, or two X's may form a part of a fused ring or a ring system.

2. A compound represented by the formula:

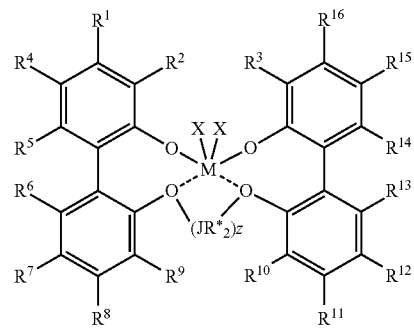

wherein the dotted line indicates a dative bond;

M is a group 4 metal;

each J is, independently, Si or Ge, provided that when z is 2 or more, one JR*s may be CR*$_2$;

z is a number from 1 to 12, provided that when z is 2, the two JR*$_2$ groups may be connected by a heteroatom, X*, to form a group represented by the formula R*$_2$J-X*-JR*$_2$;

each R* is, independently, hydrogen, a substituted C$_1$ to C$_{40}$ hydrocarbyl group, a C$_2$ to C$_{40}$ unsubstituted hydrocarbyl group, or a heteroatom, provided that any adjacent R* groups may form a fused ring or multicenter fused ring system where the rings may be aromatic, partially saturated or saturated; and each X is, independently, a substituted C$_1$ to C$_{40}$ hydrocarbyl group, a C$_1$ to C$_{40}$ unsubstituted hydrocarbyl group, a hydride, an amide, an alkoxide, a sulfide, a phosphide, a halide, an amine, a phosphine, an ether, a combination thereof, or two X's may form a part of a fused ring or a ring system;

each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, and R$^{16}$ is, independently, hydrogen, a substituted C$_1$ to C$_{40}$ hydrocarbyl group, a C$_1$ to C$_{40}$ unsubstituted hydrocarbyl group, or a heteroatom, provided that any of adjacent R groups may form a fused ring or multicenter fused ring system where the rings may be aromatic, partially saturated or saturated.

3. The compound of claim 1, wherein each of R*, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof.

4. The compound of claim 1, wherein each X is, independently, selected from Cl, Br, F, I, methyl, ethyl, propyl, butyl, pentyl, benzyl or an isomer thereof, and dimethylamido.

5. A compound represented by the formula:

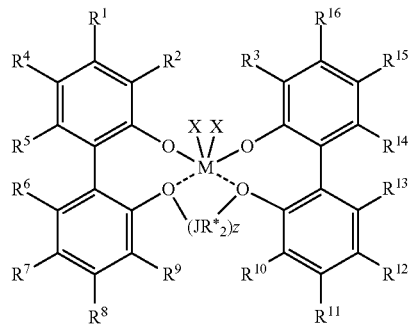

wherein the dotted line indicates a dative bond;

M is a group 4 metal;

each X is, independently, a substituted C$_1$ to C$_{40}$ hydrocarbyl group, a C$_1$ to C$_{40}$ unsubstituted hydrocarbyl group, a hydride, an amide, an alkoxide, a sulfide, a phosphide, a halide, an amine, a phosphine, an ether, a combination thereof, or two X's may form a part of a fused ring or a ring system;

each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, and R$^{16}$ is, independently, hydrogen, a substituted C$_1$ to C$_{40}$ hydrocarbyl group, a C$_1$ to C$_{40}$ unsubstituted hydrocarbyl group, or a heteroatom, provided that any of adjacent R groups may form a fused ring or multicenter fused ring system where the rings may be aromatic, partially saturated or saturated; and the (JR*$_2$)z group comprises one or more of is dicyclohexylsilyl, diphenylsilyl, di3',5'-di-tert-butylphenylsilyl, dicarbazolylsilyl, difluorenlylsilyl, cyclobutylsilyl, dicyclobutylsilyl, dicyclohexylgermyl, diphenylgermyl, di3',5'-di-tert-butylphenylgermyl, dicarbazolylgermyl difluorenlylgermyl, cyclobutylgermyl, dicyclobutylgermyl, (dicyclohexylsilyl)$_2$, (diphenylsilyl)$_2$, (di3',5'-di-tert-butylphenylsilyl)$_2$, (dicarbazolylsilyl))$_2$, (difluorenlylsilyl)$_2$, (cyclobutylsilyl)$_2$, (dicyclobutylsilyl)$_2$, (dicyclohexylgermyl)$_2$, (diphenylgermyl)$_2$, (di3',5'-di-tert-butylphenylgermyl)$_2$, (dicarbazolylgermyl)$_2$, (difluorenlylgermyl)$_2$, (cyclobutylgermyl)$_2$, and (dicyclobutylgermyl)$_2$.

6. The compound of claim 1, wherein X* is O, S, NR*$_2$ or PR*$_2$, and each R* is, independently, hydrogen, a substituted C$_1$ to C$_{40}$ hydrocarbyl group, a C$_2$ to C$_{40}$ unsubstituted hydrocarbyl group, or a heteroatom, provided that any adjacent R* groups may form a fused ring or multicenter fused ring system where the rings may be aromatic, partially saturated or saturated.

7. The compound of claim 1, wherein each of R*, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof; z is 1 or 2; and each X is, independently, selected from Cl, Br, F, I, methyl, ethyl, propyl, butyl, pentyl, benzyl or an isomer thereof, and dimethylamido.

8. The compound of claim 2, wherein wherein each of R*, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof; z is 1 or 2; and each X is, independently, selected from Cl, Br, F, I, methyl, ethyl, propyl, butyl, pentyl, benzyl or an isomer thereof, and dimethylamido.

9. A compound represented by one or more of the formulas:

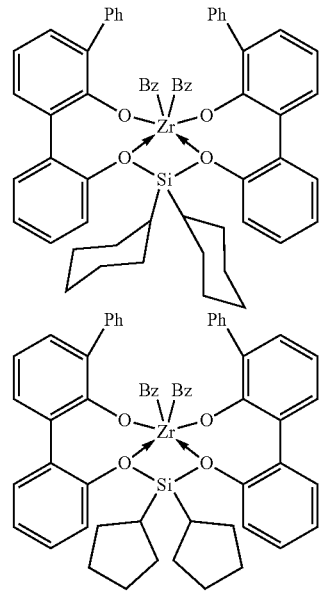

-continued
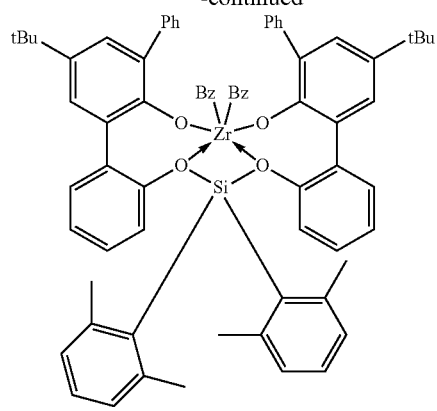
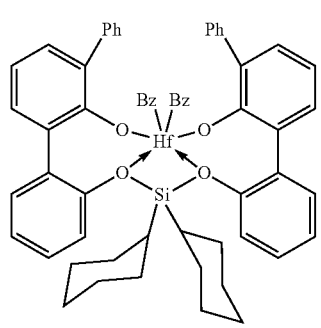
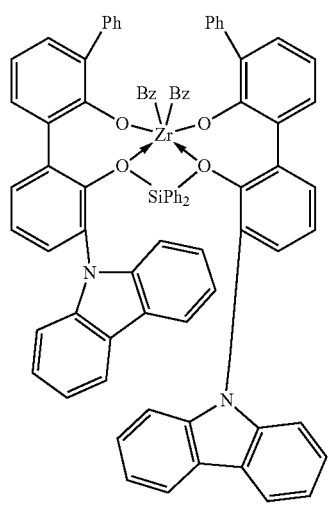
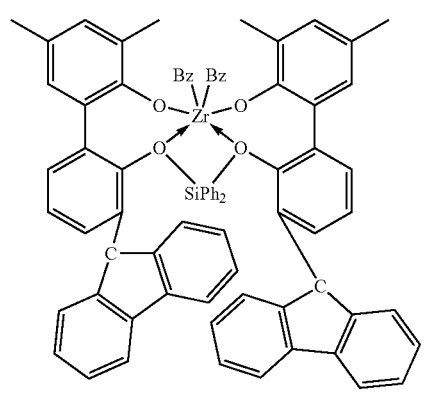
-continued
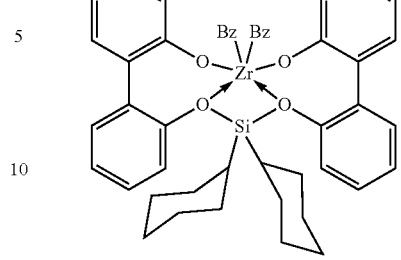
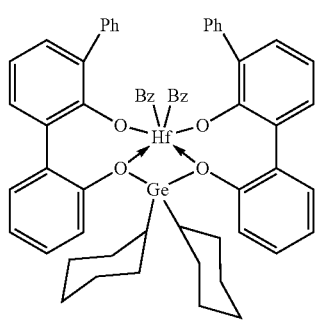
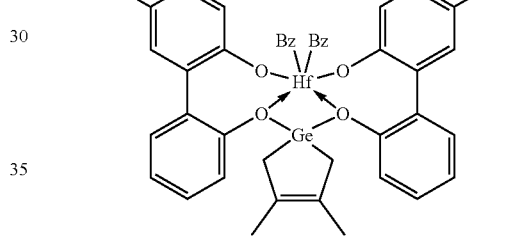
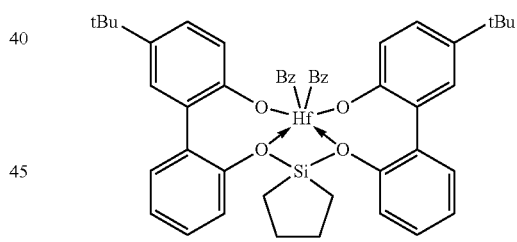
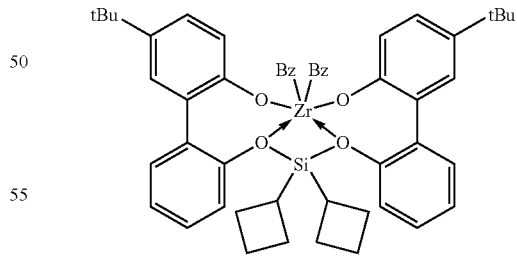
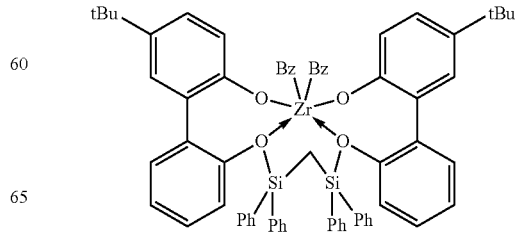

-continued

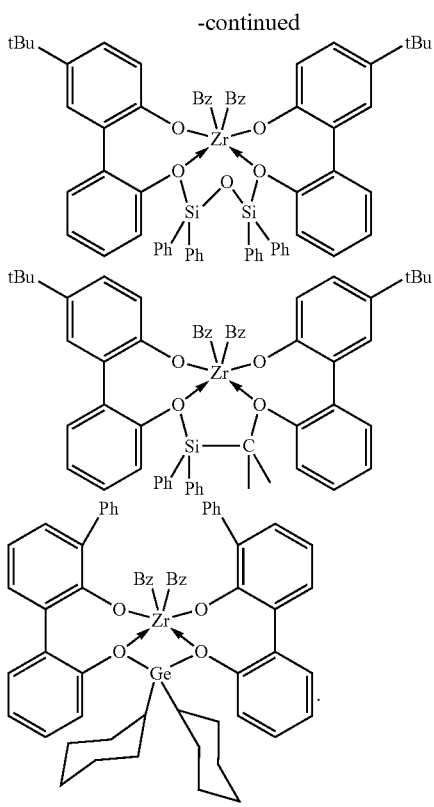

and

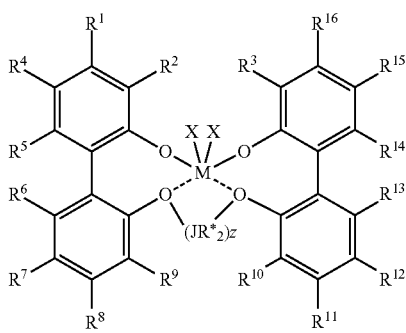

10. A catalyst system comprising activator and the catalyst compound of claim 1.

11. The catalyst system of claim 10 further comprising chain transfer agent represented by the formula $AlR_3$ or $ZnR_2$ where each R is, independently, a $C_1$-$C_8$ aliphatic radical, preferably methyl, ethyl, propyl, butyl, pentyl, hexyl, octyl, an isomer thereof, or a combination thereof.

12. The catalyst system of claim 10, wherein the activator is present on a support.

13. A catalyst system comprising activator and a compound represented by the formula:

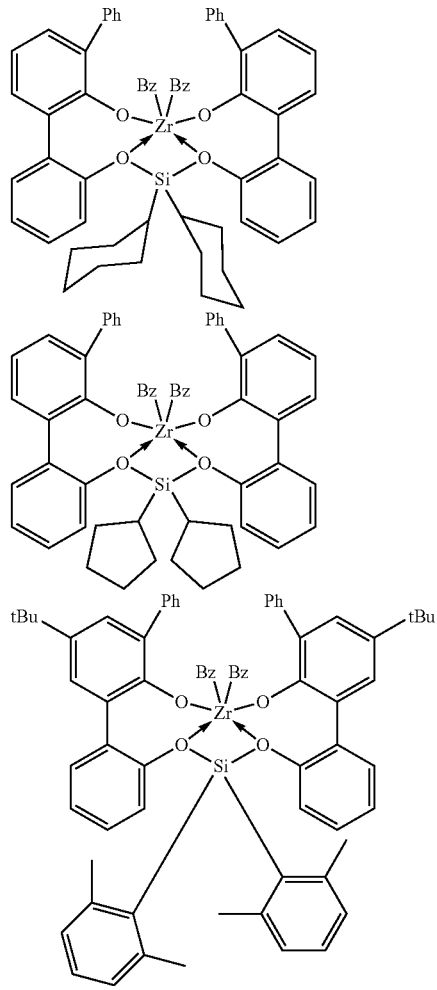

wherein
the dotted line indicates a dative bond;
M is Hf or Zr;
each J is, independently, Si or Ge, provided that when z is 2 or more one $JR*_2$ may be $CR*_2$;
z is a number from 1 to 12, provided that when z is 2, the two $JR*_2$ groups may be connected by a heteroatom, $X*$, to form a group represented by the formula $R*_2J$-$X*$-$JR*_2$;

each $R*$ is, independently, hydrogen, a substituted $C_1$ to $C_{40}$ hydrocarbyl group, a $C_2$ to $C_{40}$ unsubstituted hydrocarbyl group, or a heteroatom, provided that any adjacent $R*$ groups may form a fused ring or multi-center fused ring system where the rings may be aromatic, partially saturated or saturated; and each X is, independently, a substituted $C_1$ to $C_{40}$ hydrocarbyl group, a $C_1$ to $C_{40}$ unsubstituted hydrocarbyl group, a hydride, an amide, an alkoxide, a sulfide, a phosphide, a halide, an amine, a phosphine, an ether, a combination thereof, or two X's may form a part of a fused ring or a ring system; and each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a substituted $C_1$ to $C_{40}$ hydrocarbyl group, a $C_1$ to $C_{40}$ unsubstituted hydrocarbyl group, or a heteroatom, provided that any of adjacent R groups may form a fused ring or multicenter fused ring system where the rings may be aromatic, partially saturated or saturated.

14. The catalyst system of claim 13, wherein each of $R*$, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof; z is 1 or 2; $X*$ is O, S, $NR*_2$ or $PR*_2$; and each X is, an isomer thereof, and dimethylamido.

15. A catalyst system comprising alumoxane and one or more compounds represented by the formulas:

-continued
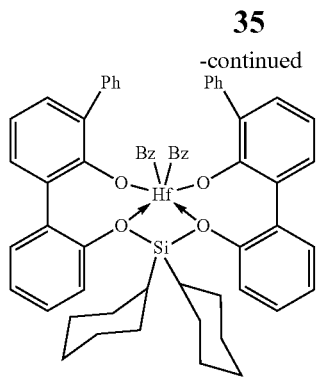
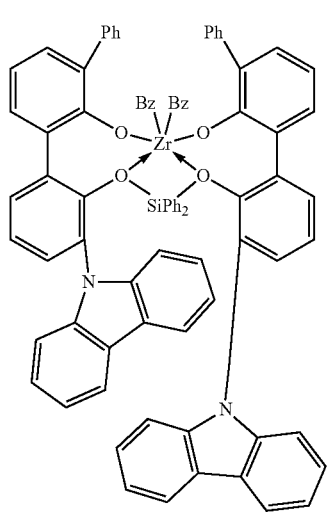
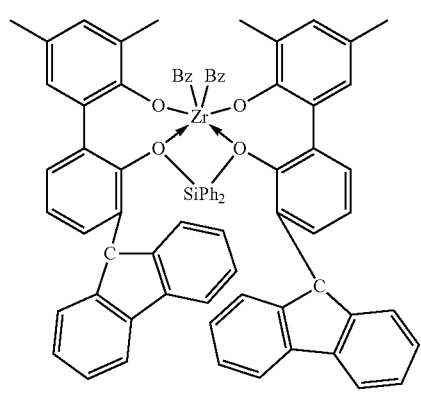
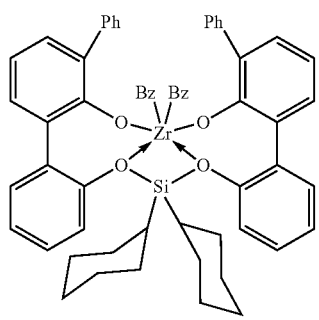
-continued
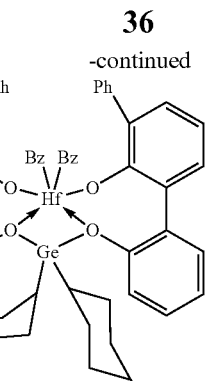
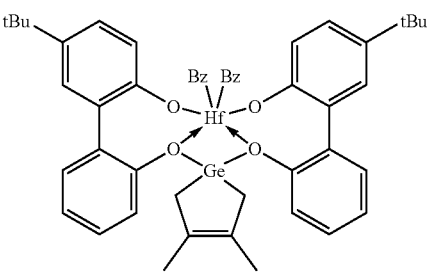
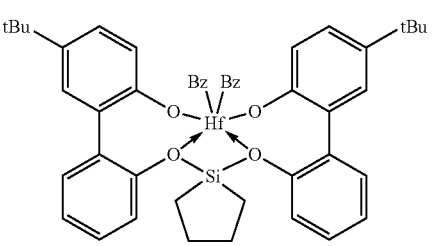
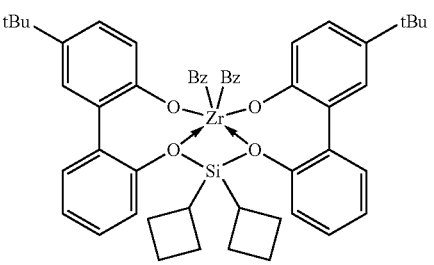
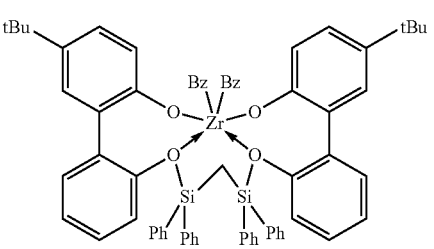
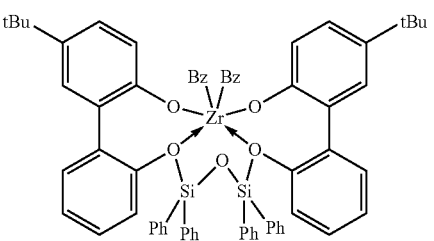

-continued

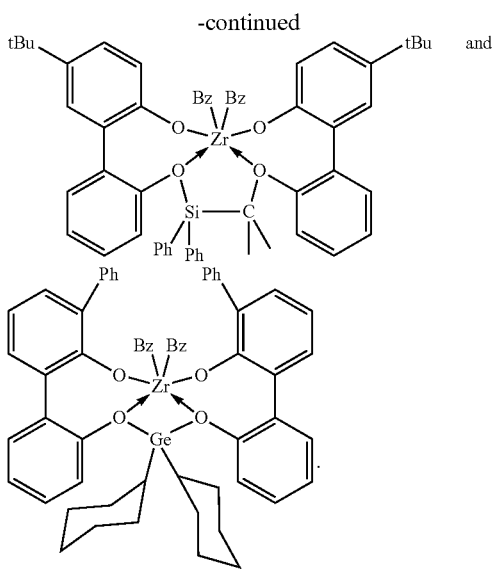

16. A process to polymerize olefins comprising contacting one or more olefins with a catalyst system comprising activator and the compound of claim 1.

17. The process of claim 16, wherein the olefins comprise ethylene and/or propylene.

18. The process of claim 16, wherein the olefins comprise $C_4$ to $C_{12}$ olefin.

19. The process of claim 16, wherein the olefins comprise norbornene, vinyl norbornene, and/or ethylidene norbornene.

20. The process of claim 16, wherein the olefins comprise cyclic comonomers.

21. The process of claim 16, wherein the activator is one or more of:
   N,N-dimethylanilinium tetrakis(pentafluorophenyl)borate,
   triphenylcarbenium tetrakis(pentafluorophenyl)borate,
   N,N-dimethylanilinium tetrakis(perfluoronaphthyl)borate,
   triphenylcarbenium tetrakis(perfluoronaphthyl)borate,
   N,N-dimethylanilinium tetrakis(perfluorobiphenyl)borate,
   N,N-diethylanilinium tetrakis(perfluorobiphenyl)borate,
   triphenylcarbenium tetrakis(perfluorobiphenyl)borate,
   N,N-diethylanilinium tetraphenylborate,
   triphenylcarbenium tetraphenylborate,
   N,N-dimethylanilinium tetrakis(pentafluorophenyl)borate,
   N,N-diethylanilinium tetrakis(pentafluorophenyl)borate,
   triphenylcarbenium tetrakis(pentafluorophenyl)borate, and
   triphenylcarbenium tetrakis(3,5-bis(trifluoromethyl)phenyl)borate).

22. The process of claim 16, wherein the process occurs at a temperature of from about 0° C. to about 300° C., at a pressure in the range of from about 0.35 MPa to about 10 MPa, and at a time of up to 300 minutes.

23. The process of claim 16 further comprising obtaining polymer.

24. The process of claim 23, wherein the polymer produced has an Mn of from 100 to 50,000 g/mol as determined by $^1$H NMR.

25. A process to polymerize olefins comprising contacting one or more olefins with a catalyst system comprising activator and a compound represented by the formula:

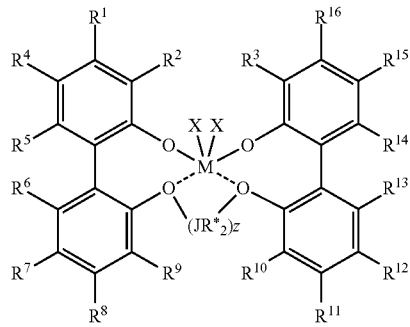

wherein
the dotted line indicates a dative bond;
M is a group 4 metal;
each J is, independently, Si or Ge, provided that when z is 2 or more one JR*s may be CR*$_2$;
z is a number from 1 to 12, provided that when z is 2, the two JR*$_2$ groups may be connected by a heteroatom, X*, to form a group represented by the formula R*$_2$J-X*-JR*$_2$;
each R* is, independently, hydrogen, a substituted $C_1$ to $C_{40}$ hydrocarbyl group, a $C_2$ to $C_{40}$ unsubstituted hydrocarbyl group, or a heteroatom, provided that any adjacent R* groups may form a fused ring or multicenter fused ring system where the rings may be aromatic, partially saturated or saturated; and
each X is, independently, a substituted $C_1$ to $C_{40}$ hydrocarbyl group, a $C_1$ to $C_{40}$ unsubstituted hydrocarbyl group, a hydride, an amide, an alkoxide, a sulfide, a phosphide, a halide, an amine, a phosphine, an ether, a combination thereof, or two X's may form a part of a fused ring or a ring system;
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, hydrogen, a substituted $C_1$ to $C_{40}$ hydrocarbyl group, a $C_1$ to $C_{40}$ unsubstituted hydrocarbyl group, or a heteroatom, provided that any of adjacent R groups may form a fused ring or multicenter fused ring system where the rings may be aromatic, partially saturated or saturated.

26. The process of claim 25, wherein each of R*, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof; z is 1 or 2; X* is O, S, NR*$_2$ or PR*$_2$; and each X is, independently, selected from Cl, Br, F, I, methyl, ethyl, propyl, butyl, pentyl, benzyl or an isomer thereof, and dimethylamido.

27. A process to polymerize olefins comprising contacting one or more olefins with a catalyst system comprising activator and a compound represented by one or more of the formulas:

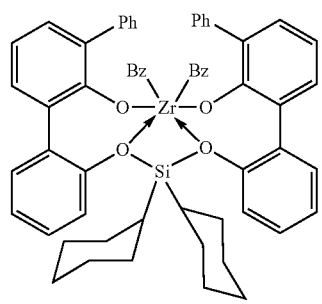

-continued
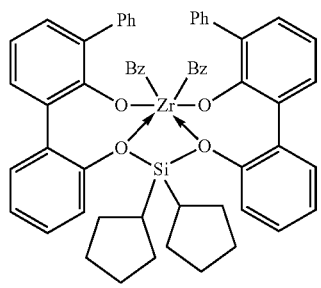
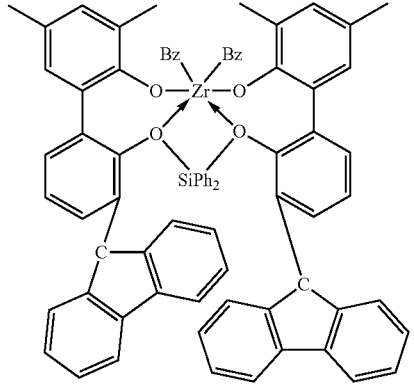
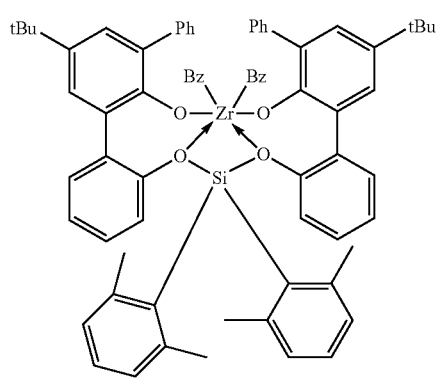
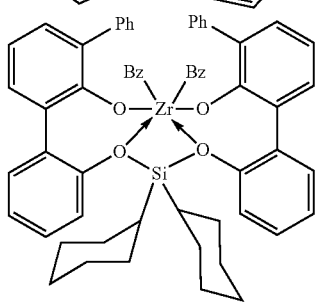
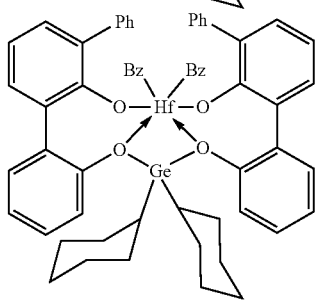
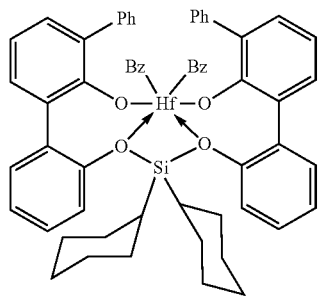
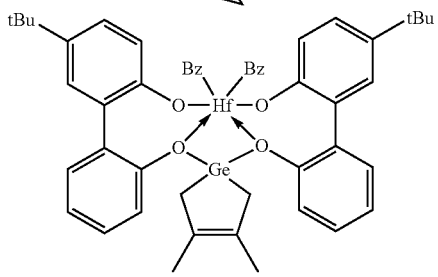
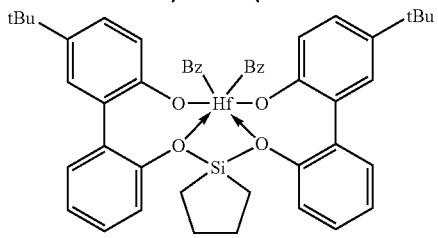
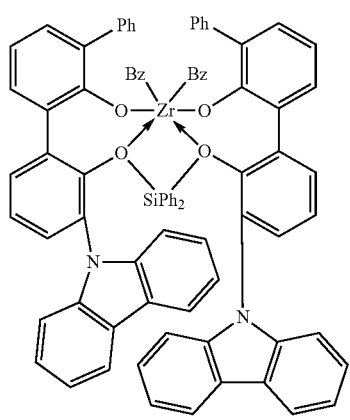
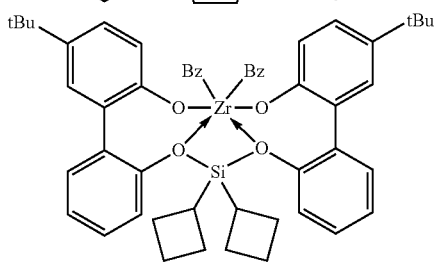

-continued

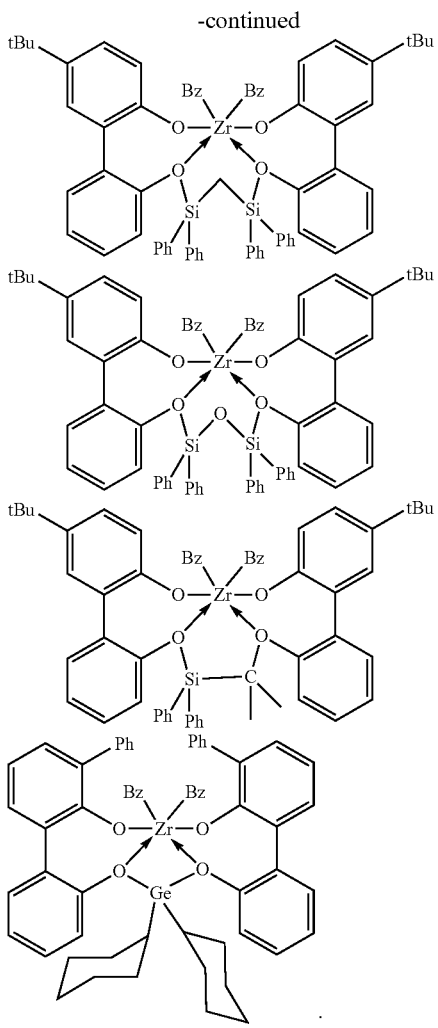

and

28. The compound of claim 2, wherein each of R*, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof.

29. The compound of claim 2, wherein each X is, independently, selected from Cl, Br, F, I, methyl, ethyl, propyl, butyl, pentyl, benzyl or an isomer thereof, and dimethylamido.

30. The compound of claim 2, wherein the $(JR*_2)z$ group comprises one or more of dicyclohexylsilyl, diphenylsilyl, di3',5'-di-tert-butylphenylsilyl, dicarbazolylsilyl, difluorenlylsilyl, cyclobutylsilyl, dicyclobutylsilyl, dicyclohexylgermyl, diphenylgermyl, di3',5'-di-tert-butylphenylgermyl, dicarbazolylgermyl difluorenlylgermyl, cyclobutylgermyl, dicyclobutylgermyl, $(dicyclohexylsilyl)_2$, $(diphenylsilyl)_2$, $(di3',5'-di-tert-butylphenylsilyl)_2$, $(dicarbazolylsilyl))_2$, $(difluorenlylsilyl)_2$, $(cyclobutylsilyl)_2$, $(dicyclobutylsilyl)_2$, $(dicyclohexylgermyl)_2$, $(diphenylgermyl)_2$, $(di3',5'-di-tert-butylphenylgermyl)_2$, $(dicarbazolylgermyl)_2$, $(difluorenlylgermyl)_2$, $(cyclobutylgermyl)_2$, and $(dicyclobutylgermyl)_2$.

31. The compound of claim 2, wherein X* is O, S, NR*$_2$ or PR*$_2$, where each R* is, independently, hydrogen, a substituted $C_1$ to $C_{40}$ hydrocarbyl group, a $C_1$ to $C_{40}$ unsubstituted hydrocarbyl group, or a heteroatom, provided that any adjacent R* groups may form a fused ring or multicenter fused ring system where the rings may be aromatic, partially saturated or saturated.

32. The compound of claim 2, wherein each of R*, is, independently, selected from the group consisting of: 1) hydrogen, ethyl, propyl, butyl, pentyl, hexyl, heptyl, octyl, nonyl, decyl, undecyl, docecyl, t-butyl, isopropyl, phenyl, napthyl, benzyl, and isomers thereof, and 2) cyclobutyl, cyclopentyl, cyclopropyl, cyclohexyl, silacyclobutyl, silacyclopropyl, germacyclobutyl, germacyclopropyl, phenyl, napthyl, and substituted versions thereof.

33. A catalyst system comprising activator and the catalyst compound of claim 2.

34. The catalyst system of claim 33 further comprising chain transfer agent represented by the formula $AlR_3$ or $ZnR_2$ where each R is, independently, a $C_1$-$C_8$ aliphatic radical, preferably methyl, ethyl, propyl, butyl, pentyl, hexyl, octyl, an isomer thereof, or a combination thereof.

35. The catalyst system of claim 33, wherein the activator is present on a support.

36. The catalyst of claim 33, wherein each of R*, is, independently, hydrogen, ethyl, propyl, butyl, pentyl, hexyl, heptyl, octyl, nonyl, decyl, undecyl, docecyl, t-butyl, isopropyl, phenyl, napthyl, benzyl, or an isomer thereof; z is 1 or 2; X* is O; and each X is, independently, selected from Cl, Br, F, I, methyl, ethyl, propyl, butyl, pentyl, benzyl or an isomer thereof, and dimethylamido.

37. The process of claim 25, wherein the olefins comprise ethylene and/or propylene.

38. The process of claim 25, wherein the olefins comprise $C_4$ to $C_{12}$ olefin.

39. The process of claim 25, wherein the olefins comprise norbornene, vinyl norbornene, and/or ethylidene norbornene.

40. The process of claim 25, wherein the olefins comprise cyclic comonomers.

41. The process of claim 25, wherein the activator is one or more of:
N,N-dimethylanilinium tetrakis(pentafluorophenyl)borate,
triphenylcarbenium tetrakis(pentafluorophenyl)borate,
N,N-dimethylanilinium tetrakis(perfluoronaphthyl)borate,
triphenylcarbenium tetrakis(perfluoronaphthyl)borate,
N,N-dimethylanilinium tetrakis(perfluorobiphenyl)borate,
N,N-diethylanilinium tetrakis(perfluorobiphenyl)borate,
triphenylcarbenium tetrakis(perfluorobiphenyl)borate,
N,N-diethylanilinium tetraphenylborate,
triphenylcarbenium tetraphenylborate,
N,N-dimethylanilinium tetrakis(pentafluorophenyl)borate,
N,N-diethylanilinium tetrakis(pentafluorophenyl)borate,
triphenylcarbenium tetrakis(pentafluorophenyl)borate, and
triphenylcarbenium tetrakis(3,5-bis(trifluoromethyl)phenyl)borate).

42. The process of claim 25, wherein the process occurs at a temperature of from about 0° C. to about 300° C., at a pressure in the range of from about 0.35 MPa to about 10 MPa, and at a time of up to 300 minutes.

43. The process of claim 25 further comprising obtaining polymer.

44. The process of claim 43, wherein the polymer produced has an Mn of from 100 to 50,000 g/mol as determined by $^1$H NMR.

45. The catalyst system of claim 10 wherein the activator comprises alumoxane and/or a non-coordinating anion.

46. The catalyst system of claim 33, wherein the activator comprises alumoxane and/or a non-coordinating anion.

47. The compound of claim 2, wherein each R* is, independently, ethyl, propyl, butyl, pentyl, hexyl, heptyl, octyl, nonyl, decyl, undecyl, docecyl, t-butyl, isopropyl, phenyl, napthyl, or an isomer thereof and z is 1, 2, 3, 4, or 5.

48. The compound of claim 2, wherein each R* is, independently, cyclobutyl, cyclopentyl, cyclopropyl, cyclohexyl, silacyclobutyl, silacyclopropyl, germacyclobutyl, germacyclopropyl, phenyl, napthyl, or a substituted version thereof and z is 1, 2, 3, 4, or 5.

* * * * *